(12) United States Patent
Csaky

(10) Patent No.: US 10,098,836 B2
(45) Date of Patent: Oct. 16, 2018

(54) METHOD FOR FORMING A MOLDED TWO-LAYER OCULAR IMPLANT

(71) Applicant: RETINA FOUNDATION OF THE SOUTHWEST, Dallas, TX (US)

(72) Inventor: Karl Csaky, Dallas, TX (US)

(73) Assignee: RETINA FOUNDATION OF THE SOUTHWEST, Dallas, TX (US)

( * ) Notice: Subject to any disclaimer, the term of this patent is extended or adjusted under 35 U.S.C. 154(b) by 0 days.

(21) Appl. No.: 14/888,387

(22) PCT Filed: May 1, 2014

(86) PCT No.: PCT/US2014/036370
§ 371 (c)(1),
(2) Date: Oct. 30, 2015

(87) PCT Pub. No.: WO2014/179568
PCT Pub. Date: Nov. 6, 2014

(65) Prior Publication Data
US 2016/0081920 A1     Mar. 24, 2016

Related U.S. Application Data

(60) Provisional application No. 61/818,568, filed on May 2, 2013.

(51) Int. Cl.
*A61K 9/00* (2006.01)
*A61K 31/26* (2006.01)
(Continued)

(52) U.S. Cl.
CPC ............. *A61K 9/0051* (2013.01); *A61F 2/14* (2013.01); *A61F 9/0017* (2013.01); *A61K 31/26* (2013.01);
(Continued)

(58) Field of Classification Search
None
See application file for complete search history.

(56) References Cited

U.S. PATENT DOCUMENTS

| 2,644,985 A | 7/1953 | Crandon et al. |
| 3,618,604 A | 11/1971 | Ness |

(Continued)

FOREIGN PATENT DOCUMENTS

| WO | 92/14450 | 9/1992 |
| WO | 97/11655 | 4/1997 |

OTHER PUBLICATIONS

Gooch, N., et al., "Ocular Drug Delivery for Glaucoma Management" Pharmaceutics (2012) 4:197-211.
(Continued)

*Primary Examiner* — Bethany P Barham
*Assistant Examiner* — Barbara S Frazier
(74) *Attorney, Agent, or Firm* — DT Ward, PC; Donna T. Ward; Mark J. Hanson

(57) ABSTRACT

The present invention generally relates to local therapies for the eye and, more particularly, to shaped controlled-release ocular implant devices, including methods for making and using such devices, for delivery of therapeutic agents to the eye. A molded two-layer ocular implant comprises a therapeutic agent for treatment or prevention of a disorder of the eye. The implant comprises a polymer layer and a silicone adhesive layer with a therapeutic agent interspersed therein and joined to the polymer layer. This implant is for placement in the sub-Tenon's space of the eye and provides sustained release of the therapeutic agent during the treatment or prevention of the disorder of the eye.

9 Claims, 9 Drawing Sheets

(51) Int. Cl.
*A61F 2/14* (2006.01)
*A61F 9/00* (2006.01)
*A61L 27/18* (2006.01)
*B29D 11/02* (2006.01)
*B29K 83/00* (2006.01)

(52) U.S. Cl.
CPC ............ *A61L 27/18* (2013.01); *B29D 11/023* (2013.01); *A61F 2210/0004* (2013.01); *A61F 2210/0076* (2013.01); *A61F 2230/0006* (2013.01); *A61F 2230/0008* (2013.01); *A61F 2240/00* (2013.01); *A61F 2240/004* (2013.01); *A61F 2250/0067* (2013.01); *A61L 2430/16* (2013.01); *B29K 2083/00* (2013.01)

(56) References Cited

U.S. PATENT DOCUMENTS

| | | |
|---|---|---|
| 3,630,200 A | 12/1971 | Higuchi |
| 3,697,629 A | 10/1972 | Bronstein |
| 3,828,777 A | 8/1974 | Ness |
| 3,845,201 A | 10/1974 | Haddad et al. |
| 3,960,150 A | 6/1976 | Hussain et al. |
| 3,986,510 A | 10/1976 | Higuchi et al. |
| 4,014,335 A | 3/1977 | Arnold |
| 4,057,619 A | 11/1977 | Higuchi et al. |
| 4,193,672 A * | 3/1980 | Trombley ............... G02C 7/04 351/159.1 |
| 4,326,306 A | 4/1982 | Poler |
| 4,391,797 A | 7/1983 | Folkman et al. |
| 4,619,662 A | 10/1986 | Juergens, Jr. |
| 4,815,690 A | 3/1989 | Shepherd |
| 4,878,910 A | 11/1989 | Koziol et al. |
| 5,158,719 A | 10/1992 | Chang et al. |
| 5,322,691 A | 6/1994 | Darougar et al. |
| 5,378,475 A | 1/1995 | Smith et al. |
| 5,443,505 A | 8/1995 | Wong et al. |
| 5,501,856 A | 3/1996 | Ohtori et al. |
| 5,507,806 A | 4/1996 | Blake |
| 5,516,522 A | 5/1996 | Peyman et al. |
| 5,645,665 A | 7/1997 | Salazar et al. |
| 5,660,851 A | 8/1997 | Domb |
| 5,674,435 A | 10/1997 | Blake |
| 5,725,493 A | 3/1998 | Avery et al. |
| 5,762,836 A | 6/1998 | Bos et al. |
| 5,773,019 A | 6/1998 | Ashton et al. |
| 5,773,021 A | 6/1998 | Gurtler et al. |
| 5,788,977 A | 8/1998 | Aguadisch et al. |
| 5,837,156 A | 11/1998 | Cumming |
| 5,902,598 A | 5/1999 | Chen et al. |
| 5,928,662 A | 7/1999 | Phillips |
| 6,159,242 A | 12/2000 | Yamasita et al. |
| 6,331,313 B1 | 12/2001 | Wong et al. |
| 6,699,493 B2 | 3/2004 | Wong |
| 6,713,081 B2 | 3/2004 | Robinson et al. |
| 6,727,277 B1 | 4/2004 | Hua et al. |
| 6,884,261 B2 | 4/2005 | Zadno-azizi et al. |
| 7,195,774 B2 | 3/2007 | Carvalho et al. |
| 7,658,364 B2 | 2/2010 | Robinson et al. |
| 8,765,166 B2 | 7/2014 | Kopczynski et al. |
| 2005/0137146 A1 | 6/2005 | Landers et al. |
| 2006/0177430 A1 | 8/2006 | Bhushan et al. |
| 2007/0190111 A1 | 8/2007 | Robinson et al. |
| 2010/0203103 A1 | 8/2010 | Dana et al. |
| 2010/0239637 A1 | 9/2010 | Ciolino et al. |
| 2013/0023838 A1 | 1/2013 | Leahy et al. |
| 2014/0031408 A1 | 1/2014 | Edelman et al. |

OTHER PUBLICATIONS

PCT International Search Report dated Sep. 17, 2015 for International Application No. PCT/US14/36370.

Extended European Search Report dated Dec. 2, 2016 issued in corresponding EP application No. 14791427.9.

Chan, J.E., T.A. Pridgen and K.G. Csaky, "Episcleral Clearance of Sodium Florescein From a Bioerodible Subtenon's Implant in the Rat" Exp Eye Res. (2010) 90(4):501-506.

Espinosa-Heidmann, D.G. et al., "Cigarette Smoke-Related Oxidants and the Development of Sub-RPE Deposits in an Experimental Animal Model of Dry AMD" IOVS (2006) 47(2):729-737.

Liu, H.S., M.F. Refojo, H.D. Perry, and D.M. Albert, "Sustained release of BCNU for the treatment of intraocular malignancies in animal models" Invest. Ophthalmol. Visual Sci. (1979) 18(10):1061-1067.

Liu, L.H.S., M.F. Refojo, C. Ni, N. Ueno, and D.M. Albert, "Sustained release of carmustine (BCNU) for treatment of experimental intraocular malignancy" British J. of Ophthalmology (1983) 67:479-484.

Japanese Office Action received in corresponding application No. 2016-512040 dated Feb. 6, 2018.

* cited by examiner

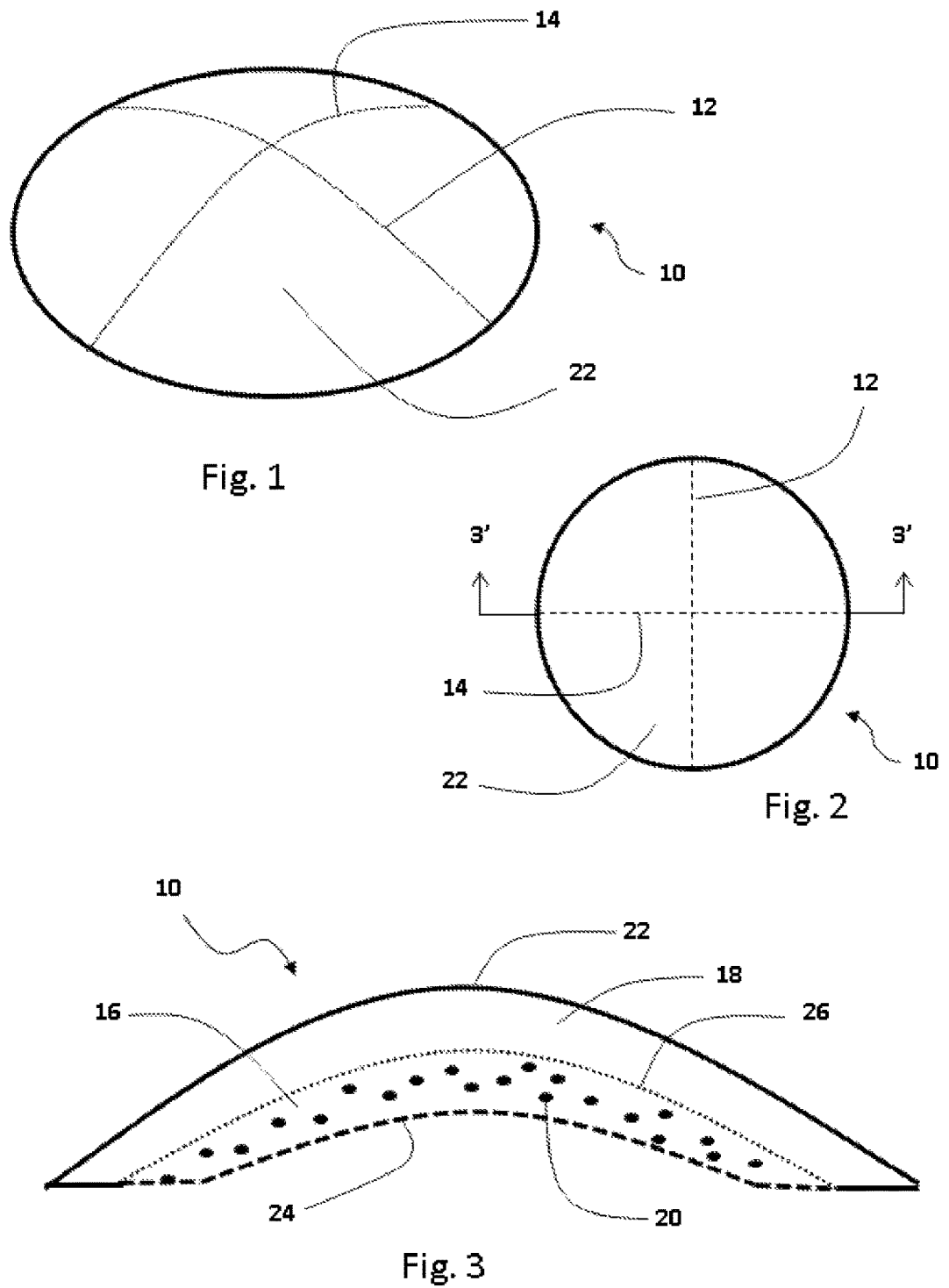

METHOD FOR FORMING A MOLDED TWO-LAYER OCULAR IMPLANT

CROSS REFERENCE TO RELATED APPLICATIONS

This application is a 35 U.S.C. § 371 U.S. National Stage Entry of International Application No. PCT/US2014/036370 filed May 1, 2014, which claims priority to U.S. Provisional Patent Application No. 61/818,568, filed May 1, 2013 entitled Two-layer ocular implant, the contents of each of which is incorporated herein by reference in its entirety.

FIELD OF THE INVENTION

The present invention generally relates to local therapies for the eye and, more particularly, to curved controlled-release ocular implant devices, including methods for making and using such devices, for delivery of therapeutic agents to the eye.

BACKGROUND OF THE INVENTION

In the treatment of many diseases and disorders of the eye, and especially in the case of degenerative or persistent conditions, implantable sustained-release delivery devices have been desired that would continuously administer a therapeutic agent to the eye for a prolonged period of time.

Local ocular implants of a wide variety of constructions and placements have been proposed heretofore for dispensing a therapeutic drug to the eye.

The present invention provides a shaped ocular implant with improved comfort and functionality.

SUMMARY OF THE INVENTION

The present invention provides a shaped ocular implant for delivery of drugs to the eye for treatment of diseases and disorders of the eye.

Various ocular implants have been described. For instance, U.S. Pat. No. 4,014,335 describes an ocular drug delivery device placed in the cul-de-sac between the sclera and lower eyelid for administering the drug and acting as a reservoir. The ocular device is characterized therein as administering drug to the eye in a controlled, continuous dosage rate over a prolonged time. To accomplish this, the ocular device comprises a three-layered laminate of polymeric materials holding the drug in a central reservoir region of the laminate. The drug diffuses from the reservoir through at least one of the polymeric layers of the laminate.

U.S. Pat. No. 5,773,021 describes bioadhesive ophthalmic inserts that are placed in the conjunctival sac, in which the inserts are prepared by extrusion, thermoforming, or heat compression of a polymeric material matrix and the drug to be delivered. The polymeric matrix comprises a water-soluble biocompatible polymer, such as hydroxyalkyl celluloses, maltodextrins, chitosans, modified starches or polyvinyl alcohols; a water-insoluble biocompatible polymer such as an alkyl cellulose; and where applicable a bioadhesive polymer such as polyvinyl carboxylic acid type polymers or certain bioadhesive polysaccharides or derivatives thereof. The ophthalmic inserts are characterized therein as intended for the prolonged and controlled release of a medicinal substance.

U.S. Pat. No. 5,773,019 describes a continuous release drug delivery implant which, among other mentioned places, can be mounted either on the outer surface of the eye or within the eye. A drug core is covered by a polymer coating layer that is permeable to the low solubility agent without being release rate limiting. Descriptions include a coating of cyclosporine A (CsA) drug cores with one or multiple coatings of polyvinyl alcohol solution, followed by heating to 104, 110 or 120° C., presumably to cross link and harden the coating(s) in place around the core. Also described is an implant prepared by fixing a pellet directly over a smaller hole formed in a silicone film, followed by a suture being placed around the pellet in a gapped relationship thereto, and then the entire assembly is coated again with silicone to form the implant. The ocular device is characterized therein as giving a continuous release to an affected area, once implanted, and producing long-term sustained tissue and vitreous levels at relatively low concentrations.

U.S. Pat. No. 5,378,475 describes a sustained-release implant for insertion into the vitreous cavity of the eye. The implant has a first impermeable coating, such as ethylene vinyl acetate, surrounding most, but not all, of a drug reservoir and a second permeable coating, such as a permeable crosslinked polyvinyl alcohol, disposed over the first coating including the region where the first coating does not cover the drug reservoir, to provide a location through which the drug can diffuse out of the implant. The implant also has a tab, which can be used to suture the device in place in the eye. The implant devices are prepared by applying coating solutions, such as by dipping, spraying or brushing, of the various coating layers around the drug reservoir.

U.S. Pat. No. 5,725,493 describes an ocular implant device for providing drugs to the vitreous cavity over a period of time. The drug reservoir is attached to the outside of the eye with a passageway permitting medicament to enter the vitreous cavity of the eye.

U.S. Pat. Nos. 6,713,081 and 7,658,364 describe dual mode and singular mode ocular therapeutic agent delivery devices. These devices are suitable for subconjunctival and intravitreal placement.

The above-listing of publications describing prior ocular implant systems is intended to be only illustrative in nature, and not exhaustive.

Local ocular implants avoid the shortcomings and complications that can arise from systemic therapies of eye disorders. For instance, oral therapies for the eye fail to provide sustained-release of the drug into the eye. Instead, oral therapies often only result in negligible actual absorption of the drug in the ocular tissues due to low bioavailability of the drug. Ocular drug levels following systemic administration of drugs is usually limited by various blood/ocular barriers (i.e., tight junctions between the endothelial cells of the capillaries). These barriers limit the amounts of drugs entering the eye via systemic circulation. In addition, variable gastrointestinal drug absorption and/or liver metabolism of the medications can lead to dosage-dependent and inter-individual variations in vitreous drug levels. Moreover, adverse side effects have been associated with systemic administration of certain drugs to the eyes.

For instance, systemic treatments of the eye using the immune response modifier cyclosporine A (CsA) have the potential to cause nephrotoxicity or increase the risk of opportunistic infections, among other concerns. This is unfortunate since CsA is a recognized effective active agent for treatment of a wide variety of eye diseases and indications, such as endogenous or anterior uveitis, corneal transplantation, Behçet's disease, vernal or ligneous keratoconjunctivitis, dry eye syndrome, and the like. In addition, rejection of corneal allografts and stem cell grafts occurs in up to 90% of patients when associated with risk factors such as corneal neovascularization. CsA has been identified as a possibly useful drug for reducing the failure rate of such surgical procedures for those patients. Thus, other feasible delivery routes for such drugs that can avoid such drawbacks associated with systemic delivery are in demand.

Apart from implant therapies, other local administration routes for the eye have included topical delivery. Such therapies include ophthalmic drops and topical ointments containing the medicament. Tight junctions between corneal epithelial cells limit the intraocular penetration of eye drops and ointments. Topical delivery to the eye surface via solutions or ointments can in certain cases achieve limited, variable penetration of the anterior chamber of the eye. However, therapeutic levels of the drug are not achieved and sustained in the middle or back portions of the eye. This is a major drawback, as the back (posterior) chamber of the eye is a frequent site of inflammation or otherwise the site of action where, ideally, ocular drug therapy should be targeted for many indications.

Therapeutic agents for the treatment of the eye can be broadly divided into two groups: hydrophilic compounds and lipophilic compounds. Hydrophilic compounds are well established and have a wide range of therapeutic uses due to the ease with which they dissolve in water. However, hydrophilic compounds do not cross lipid barriers easily and, in the eye specifically, lymphatic clearance of compounds in the episclera contributes to the difficulty of maintaining therapeutic levels of the drug as mentioned herein.

Lipophilic compounds do not dissolve easily in an aqueous solution, but due to their chemical nature may easily cross lipid membranes including the blood-neural barrier in the brain or the blood-retinal barrier in the eye. Therefore, lipophilic compounds represent an emerging class of therapeutic drugs that may circumvent difficulties seen in existing drug treatment methodologies. In some embodiments, the lipophilic agents or drugs employed in the implants of the invention collect, concentrate, aggregate or otherwise have an increased concentration in retinal tissues. This retinal trapping or sink effect provides for increased efficacy. Such efficacy may be measured by an increase in one or more phenotypic effects, half-life of the drug at a particular retinal or retinal-related location or durational clinically beneficial effect.

In some embodiments retinal trapping results in an increase of drug substance of at least 10%, 20%, 30%, 40%, 50%, 60%, 70%, or 80% or more of drug to the retinal tissue or cells. In some embodiments, the ratio of drug in the retinal tissue, e.g., retinal trap, compared to either surrounding tissue or drug remaining in the implant at any time is 1.5 to 1, 2 to 1, 3 to 1, 4 to 1 or greater than 5 to 1.

Age-related macular degeneration (AMD) is a common disease associated with aging that gradually impairs sharp, central vision. There are two common forms of AMD: dry AMD and wet AMD. About ninety percent of the cases of AMD are the dry form, caused by degeneration and thinning of the tissues of the macula; a region in the center of the retina that allows people to see straight ahead and to discern fine details. Although only about ten percent of people with AMD have the wet form, it poses a much greater threat to vision. With the wet form of the disease, rapidly growing abnormal blood vessels known as choroidal neovascular membranes (CNVM) develop beneath the macula. These vessels leak fluid and blood that destroy light sensing cells, thereby producing blinding scar tissue, with resultant severe loss of central vision. Wet AMD is the leading cause of legal blindness in the United States for people aged sixty-five or more with approximately 25,000 new cases diagnosed each year in the United States. Ideally, treatments of the indication would include inducing an inhibitory effect on the choroidal neovascularization (CNV) associated with AMD. The macula is located at the back of the eye and therefore treatment of CNVM by topical delivery of pharmacological agents to the tissues of the macula tissues is not possible. Intravitreal injections of anti-angiogenic agents, laser photocoagulation, photodynamic therapy, and surgical removal are currently used to treat CNVM. Unfortunately, the recurrence rate using such methods exceeds 50-90% in some cases. In most cases indefinite treatment is required.

As an approach for circumventing the barriers encountered by local topical delivery, one local therapy route for the eye has involved direct intravitreal injection of a treatment drug through the sclera (i.e., the spherical, collagen-rich outer covering of the eye). However, the intravitreal injection delivery route tends to result in a short half-life and rapid clearance without sustained release capability being attained. Consequently, weekly to monthly injections are frequently required to maintain therapeutic ocular drug levels. This is not practical for many patients.

Given these drawbacks, the use of implant devices placed in or adjacent to the eye tissues to deliver therapeutic drugs thereto should offer a great many advantages and opportunities over the rival therapy routes. Despite the variety of ocular implant devices which have been described and used in the past, the full potential of the therapy route has not been realized. Among other things, prior ocular implant devices deliver the drug to the eye tissues via a single mode of administration for a given treatment, such as via slow constant rate infusion at low dosage. However, in many different clinical situations, such as with CNVM in AMD, this mode of drug administration might be a sub-optimal ocular therapy regimen.

Another problem exists with previous ocular implants, from a construction standpoint, insofar as preparation techniques thereof have relied on covering the drug pellet or core with a permeable polymer by multi-wet coating and drying approaches. Such wet coating approaches can raise product quality control issues such as an increased risk of delamination of the thinly applied coatings during subsequent dippings, as well as thickness variability of the polymer around the drug pellets obtained during hardening. Additionally, increased production costs and time from higher rejection rates and labor and an increased potential for device contamination from additional handling are known problems with present implant technology.

Accordingly, certain aspects of the present invention provide local treatment of a variety of eye diseases. Other aspects of the present invention also provide a method for the delivery of pharmaceuticals to the eye to effectively treat eye disease, while reducing or eliminating the systemic side effects of these drugs. Certain aspects of the present invention also provide shaped sustained-release ocular implants for administration of therapeutic agents to the eye for prolonged periods of time. Additionally, certain aspects of the present invention provide approaches to alter the areas of the eye that are affected by diffusion of drugs from sustained-release ocular implants. Certain aspects of the present invention also provide methods for making shaped ocular implants with reduced product variability.

Other aspects of the present invention also provide methods for making shaped ocular implants well-suited for ocular treatment trials using animal models. Other advantages and benefits of aspects of the present invention will be apparent from consideration of the present specification.

In these and other ways described below, the inventive implants offer a myriad of advantages, improvements, benefits, and therapeutic opportunities. The inventive implants are highly versatile and can be tailored to enhance the delivery regimen both in terms of administration mode(s) and type(s) of drugs delivered. The implants of this invention permit continuous release of therapeutic agents into the eye over a specified period of time, which can be weeks, months, or even years as desired. As another advantage, the inventive implant systems of this invention require intervention only for initiation and termination of the therapy (i.e., removal of the implant). Patient compliance issues during a regimen are eliminated. The time-dependent delivery of one or more drugs to the eye by this invention makes it possible to maximize the pharmacological and physiological effects of the eye treatment. The inventive implants have human and veterinary applicability.

In one aspect of the present invention, there is provided a method for forming a molded two-layer ocular implant, the implant comprising a therapeutic agent for treatment or prevention of a disorder of the eye, the method comprising: a) dispensing a polymer into a curved depression on a mold body to form a polymer layer having a curved external surface in contact with the bottom of the curved depression and further comprising an exposed upper surface; b) generating a curvature in the exposed upper surface of the polymer layer, thereby forming a curved polymer layer interface surface; c) curing the polymer layer, thereby providing a hardened curved polymer layer interface surface; d) dispensing a silicone adhesive comprising the therapeutic agent dispersed therein onto the hardened interface surface to provide a silicone layer with an exposed surface; e) generating a curvature in the exposed surface of the silicone layer thereby forming a curved eye-contacting surface; and f) curing the silicone layer such that the first layer and second layer are fixed to each other, thereby forming the molded two-layer ocular implant.

Another aspect of the present invention is a method for forming a molded two-layer ocular implant, the implant comprising a therapeutic agent for treatment or prevention of a disorder of the eye, the method comprising: a) dispensing a polymer into a curved depression on a first mold body to form a polymer layer having a curved external surface in contact with the bottom of the curved depression and further comprising an exposed upper polymer surface; b) generating a curvature in the exposed upper surface of the polymer layer, thereby forming a curved polymer layer interface surface; c) curing the polymer layer to produce a cured polymer layer, d) dispensing a silicone adhesive comprising the therapeutic agent dispersed therein into second curved depression on a second mold body to provide a silicone layer with a curved silicone layer interface surface in contact with the bottom of the curved depression and further comprising an exposed upper silicone surface; e) generating a curvature in the exposed silicone surface, thereby forming a curved eye-contacting surface; f) curing the silicone layer to produce a cured silicone layer; and g) joining the cured polymer layer to the cured silicone layer by attachment of the polymer layer interface surface to the silicone layer interface surface with biocompatible adhesive. In certain embodiments, the adhesive is pressure sensitive. In certain embodiments, the pressure sensitive adhesive may comprise any of those from DOW CORNING® such as BIO-PSA 7-4302 or other such adhesives from the DOW CORNING® catalog, the contents of which are incorporated herein by reference in their entirety.

In certain embodiments, the implant is circular or oval-shaped.

In certain embodiments, steps b) and e) are performed using an impression body with a curved protrusion for generating the curvature in the exposed surface of the polymer layer and the exposed surface of the silicone layer.

In certain embodiments, step b) is performed using a first impression body comprising a first curved protrusion for generating the curvature in the exposed surface of the polymer layer and step e) is performed using a second impression body comprising a second curved protrusion for generating the curvature in the exposed surface of the silicone layer, wherein the curvature dimensions of the first and second curved protrusions are different.

In certain embodiments, the polymer layer is resistant to diffusion of the therapeutic agent from the silicone layer.

In certain embodiments, the polymer layer is substantially impermeable to diffusion of the therapeutic agent from the silicone layer.

In certain embodiments, the polymer is polyvinyl acetate, cross-linked polyvinyl alcohol, cross-linked polyvinyl butyrate, ethylene ethylacrylate co-polymer, polyethyl hexylacrylate, polyvinyl chloride, polyvinyl acetals, plasiticized ethylene vinylacetate copolymer, polyvinyl alcohol, polyvinyl acetate, ethylene vinylchloride copolymer, polyvinyl esters, polyvinylbutyrate, polyvinylformal, polyamides, polymethylmethacrylate, polybutylmethacrylate, plasticized polyvinyl chloride, plasticized nylon, plasticized soft nylon, plasticized polyethylene terephthalate, natural rubber, polyisoprene, polyisobutylene, polybutadiene, polyethylene, polytetrafluoroethylene, polyvinylidene chloride, polyacrylonitrile, cross-linked polyvinylpyrrolidone, polytrifluorochloroethylene, chlorinated polyethylene, poly(1,4'-isopropylidene diphenylene carbonate), vinylidene chloride, acrylonitrile copolymer, vinyl chloride-diethyl fumarate copolymer, silicone rubbers, medical grade polydimethylsiloxanes, ethylene-propylene rubber, silicone-carbonate copolymers, vinylidene chloride-vinyl chloride copolymer, vinyl chloride-acrylonitrile copolymer or vinylidene chloride-acrylonitride copolymer.

In certain embodiments, the polymer layer and the silicone layer are each about 1 mm thick.

In certain embodiments, the polymer layer and/or the silicone layer further comprise an agent that blocks lymphatic absorption of the therapeutic agent.

In certain embodiments, the silicone layer further comprises an ophthalmic permeation agent that increases ocular permeability of the therapeutic agent into the eye.

In certain embodiments, the ophthalmic permeation agent is methylsulfonylmethane.

In certain embodiments, the radius of curvature of the curved eye-contacting surface of the silicone layer ranges from between about 5 mm to about 6 mm.

In certain embodiments, the resulting molded implant is circular with a diameter ranging between about 1 mm and 8 mm.

In certain embodiments, the resulting molded implant is circular with a diameter ranging between about 1 mm and 3 mm.

In certain embodiments, the therapeutic agent is a nuclear factor (erythroid-derived 2)-like 2 enhancer (Nrf2 regulator).

In certain embodiments, the Nrf2 regulator is sulforaphane.

In certain embodiments, the therapeutic agent is selected from the group consisting of fumagillin analogs, minocycline, fluoroquinolone, cephalosporin antibiotics, herbimycon A, tetracycline, chlortetracycline, bacitracin, neomycin, polymyxin, gramicidin, oxytetracycline, chloramphenicol, gentamicin, erythromycin, antibacterial agents, sulfonamides, sulfacetamide, sulfamethizole, sulfoxazole, nitrofurazone, sodium propionate, antiviral agents, idoxuridine, famvir, trisodium phosphonoformate, trifluorothymidine, acyclovir, ganciclovir, DDI, AZT, protease and integrase inhibitors, anti-glaucoma agents, beta blockers, timolol, betaxolol, atenolol, prostaglandin analogues, hypotensive lipids, carbonic anhydrase inhibitors, antiallergenic agents, antazoline, methapyriline, chlorpheniramine, pyrilamine, prophenpyridamine, anti-inflammatory agents, hydrocortisone, leflunomide, dexamethasone phosphate, fluocinolone acetonide, medrysone, methylprednisolone, prednisolone phosphate, prednisolone acetate, fluoromethalone, betamethasone, triamcinolone acetonide, adrenalcortical steroids and their synthetic analogues, 6-mannose phosphate, antifungal agents, fluconazole, amphotericin B, liposomal amphotericin B, voriconazole, imidazole-based antifungals, tiazole antifungals, echinocandin-like lipopeptide antibiotics, lipid formulations of antifungals, polycations, polyanions, suramine, protamine, decongestants, phenylephrine, naphazoline, tetrahydrazoline, anti-angiogenesis compounds including those that can be potential anti-choroidal neovascularization agents, 2-methoxyestradiol and its analogues, 2-propynl-estradiol, 2-propenyl-estradiol, 2-ethoxy-6-oxime-estradiol, 2-hydroxyestrone, 4-methoxyestradiol, VEGF antagonists, VEGF antibodies and VEGF antisense compounds, angiostatic steroids, anecortave acetate and its analogues, 17-ethynylestradiol, norethynodrel, medroxyprogesterone, mestranol, androgens with angiostatic activity, ethisterone, thymidine kinase inhibitors, adrenocortical steroids and their synthetic analogues, fluocinolone acetonide, triamcinolone acetonide, immunological response modifying agents, cyclosporineA, Prograf (tacrolimus), macrolide immunosuppressants, mycophenolate mofetil, rapamycin, muramyl dipeptide, vaccines, anti-cancer agents, 5-fluorouracil, platinum coordination complexes, cisplatin, carboplatin, adriamycin, antimetabolites, methotrexate, anthracycline antibiotics, antimitotic drugs, paclitaxel, docetaxel, epipdophylltoxins, etoposide, nitrosoureas, carmustine, alkylating agents, cyclophosphamide, arsenic trioxide, anastrozole, tamoxifen citrate, triptorelin pamoate, gemtuzumab ozogamicin, irinotecan hydrochloride, leuprolide acetate, bexarotene, exemestrane, epirubicin hydrochloride, ondansetron, temozolomide, topoteanhydrochloride, tamoxifen citrate, irinotecan hydrochloride, trastuzumab, valrubicin, gemcitabine HCl, goserelin acetate, capecitabine, aldesleukin, rituximab, oprelvekin, interferon alfa-2a, letrozole, toremifene citrate, mitoxantrone hydrochloride, irinotecan HeL, topotecan HCl, etoposide phosphate, amifostine, antisense agents, antimycotic agents, miotic and anticholinesterase agents, pilocarpine, eserine salicylate, carbachol, diisopropyl fluorophosphate, phospholine iodine, demecarium bromide, mydriatic agents such as atropine sulfate, cyclopentane, homatropine, scopolamine, tropicamide, eucatropine, hydroxyamphetamine, differentiation modulator agents, sympathomimetic agents epinephrine, anesthetic agents, lidocaine, benzodiazepam, vasoconstrictive agents, vasodilatory agents, polypeptides, protein agents, angiostatin, endostatin, matrix metalloproteinase inhibitors, platelet factor 4, interferon-gamma, insulin, growth hormones, insulin related growth factor, heat shock proteins, humanized antiIL2 receptor mAb (Daclizumab), etanercept, mono and polyclonal antibodies, cytokines, antibodies to cytokines, neuroprotective agents such as calcium channel antagonists including nimodipine and diltiazem, neuroimmunophilin ligands, neurotropins, memantine, NMDA antagonists, acetylcholinesterase inhibitors, estradiol and analogues, vitamin B12 analogues, alpha-tocopherol, NOS inhibitors, antioxidants, glutathione, superoxide dismutase, cobalt, copper, neurotrophic receptors, Akt kinase, growth factors, nicotinamide (vitamin B3), alpha-tocopherol (vitamin E), succinic acid, dihydroxylipoic acid, fusidic acid, cell transport/mobility impending agents, colchicine, vincristine, cytochalasin B, carbonic anhydrase inhibitor agents, integrin antagonists and lubricating agents.

In certain embodiments, the therapeutic agent is a lipophilic agent. In certain embodiments, the lipophilic therapeutic agent is selected from the group consisting of Idebenone, rapamycin, 2-cyano-3,12 dioxooleana-1,9 dien-28-imidazolide (CDDO-Im), 2-cyano-3,12-dioxooleana-1,9(11)-dien-28-oic acid-ethyl amide (CDDO-ethyl amide), and 2-cyano-3,12-dioxooleana-1,9(11)-dien-28-oic acid trifluoroethyl amide (CDDO-TFEA).

In certain embodiments, the polymer layer and/or the silicone layer further comprise a nutraceutical oil.

In certain embodiments, the nutraceutical oil is omega-3 fish oil.

In certain embodiments, the silicone layer further comprises an excipient that improves the release of drug.

In certain embodiments, the excipient is selected from one or more of isopropyl myristate, levomenthol, propylene and tetraglycol.

Another aspect of the invention is a two-layer implant formed by the methods described herein. The implant of certain embodiments may be used for implantation into the sub-Tenon's space of a human. The implant of other embodiments may be used for implantation into the sub-Tenon's space of a rodent.

Another aspect of the invention is a molded two-layer ocular implant comprising a therapeutic agent for treatment or prevention of a disorder of the eye, the implant comprising: a first hardened layer comprising a polymer, the first hardened layer comprising curvature at both surfaces; and a second hardened layer comprising a silicone adhesive and the therapeutic agent, the second hardened layer and comprising curvature at both surfaces.

In certain embodiments, the curvature of one surface of the first hardened layer and the curvature of one surface of the second layer are both formed using an impression body with a curved protrusion.

In certain embodiments, the first and second hardened layers are defined as follows: the curvature of a first surface of the first hardened layer is formed by dispensing the polymer into a mold body; the curvature of a second surface of the first hardened layer is formed by a first curved protrusion on a first impression body; the curvature of a first surface of the second hardened layer is formed by dispensing the silicone adhesive onto the curvature of the second surface of the first hardened layer; and the curvature of a second surface of the second hardened layer is formed by a second curved protrusion on a second impression body.

In certain embodiments, the first hardened layer is resistant to diffusion of the therapeutic agent from the second hardened layer.

In certain embodiments, the first hardened layer is substantially impermeable to diffusion of the therapeutic agent from the second hardened layer.

Another aspect of the present invention is a mold assembly for forming a two-layer ocular implant, the mold assembly comprising: a mold body comprising a contact surface with a curved depression formed therein for forming a first curved surface of a polymer layer of the implant; and an impression body comprising a curved protrusion for forming curvature at a second surface of the polymer layer and for forming curvature in a surface of a silicone adhesive layer of the implant.

In certain embodiments, the curved protrusion is for forming curvature in only the second surface of the polymer layer of the implant and the mold assembly further comprises a second impression body comprising a second curved protrusion for forming the curvature in the surface of the silicone adhesive layer of the implant.

In certain embodiments, the impression body is mounted on a support frame configured to allow vertical movement of the impression body and the support frame while the mold body remains stationary and the support frame further comprises a means for locking of the position of the impression body.

In certain embodiments, the mold assembly further comprises a means for controlling the thickness of the polymer layer and the silicone adhesive layer formed by the mold body and impression body.

In certain embodiments, the mold body is cylindrical and dimensioned for insertion in a centrifuge tube.

In certain embodiments, the surfaces of the depression and the protrusion are coated with a non-stick material to facilitate removal of the implant from the mold body.

In certain embodiments, the non-stick material is Teflon® or aluminum.

Another aspect of the present invention is a method for determining the effectiveness of the implant as described herein for treatment or prevention of macular degeneration in a rodent, the method comprising: a) placing the implant as described herein in the sub-Tenon's space of the eye of the rodent, wherein the rodent is fed with high-fat chow supplemented with hydroquinone; and b) monitoring the release of the drug over time by examining the eye of the rodent with histology, electroretinography or changes in gene expression the retinal pigment epithelium or photoreceptors, thereby indicating the effectiveness of the implant against macular degeneration.

Another aspect of the present invention is a method for evaluating the effectiveness of the implant as described herein for treatment or prevention of macular degeneration in a human, the method comprising: a) placing the implant as described herein into the sub-Tenon's space of the eye of the human; and b) examining the eye of the human using a technique selected from the group consisting of: 2 color (blue, red) microperimetry, low luminance visual acuity, multi-focal electroretinography, dynamic perimetry, color vision assessment, photo-stress testing and static perimetry, thereby evaluating the effectiveness of the implant against macular degeneration.

Another aspect of the present invention is a kit for preparing a molded two-layer composite ocular implant comprising a therapeutic agent for treatment or prevention of a disorder of the eye, the kit comprising: a) a mold assembly for molding the implant; b) a silicone adhesive comprising a therapeutic agent for forming a first layer; and c) a polymer for forming a second layer.

In certain embodiments, the mold assembly of the kit is the mold assembly described herein which includes a single impression body. In other embodiments, the mold assembly of the kit is the mold assembly which includes two impression bodies.

In certain embodiments, the kit further comprises instructions for making a molded two-layer silicon composite ocular implant by sequential layering of the polymer and the silicone adhesive comprising the therapeutic agent.

BRIEF DESCRIPTION OF THE FIGURES

FIG. 1. A perspective view of an implant according to one embodiment of the invention with curved lines 12 and 14 showing the curvature of the upper surface of the implant.

FIG. 2. A top view of the implant of FIG. 1.

FIG. 3: A cross sectional side view of the implant of FIGS. 1 and 2 taken along line 3'-3' of FIG. 2 (along dotted line 14) showing the lower layer 16 and upper layer 18 of the implant with drug particles 20 dispersed in the lower layer 16. Features of the implant are omitted for clarity.

DETAILED DESCRIPTION OF THE INVENTION

Overview

Figure 4:
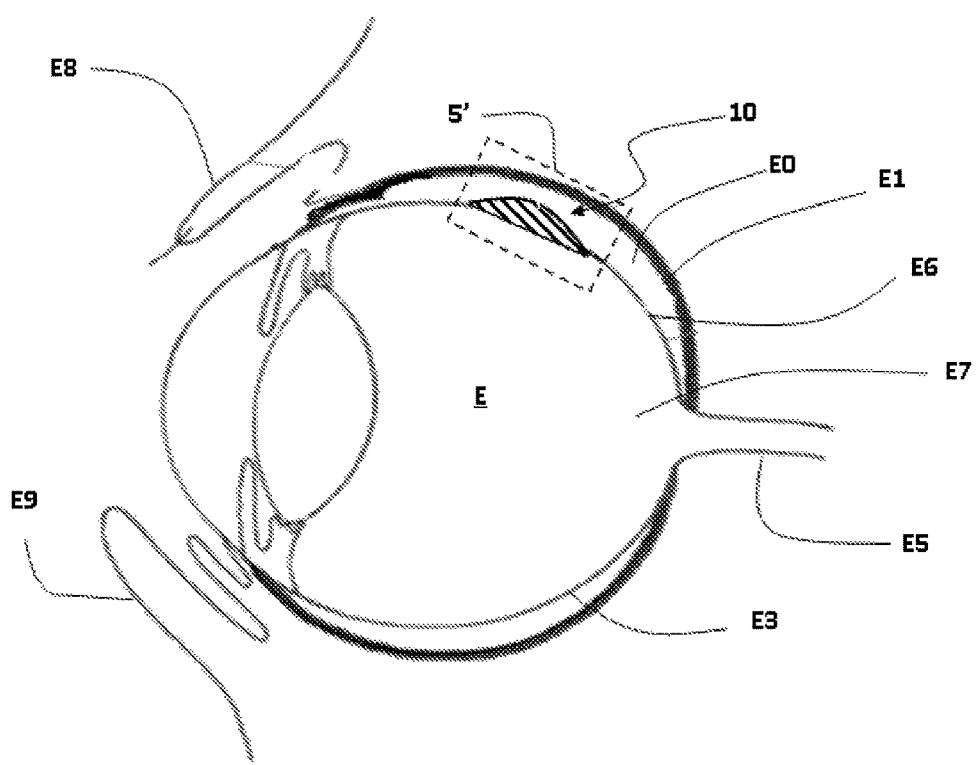
FIG. 4. A schematic side slice view showing selected anatomy of an eye E with the placement of a perspective view of the implant of FIGS. 1-3 in the sub-Tenon's space E0. Other structures of the eye E are shown for context.

The present invention provides a molded composite ocular implant comprising a therapeutic agent for treatment or prevention of a disorder of the eye. Also provided are methods of making the silicone composite ocular implant and using the implant for treatment of various diseases or disorders of the eye, including tests of the implant with experimental animals such as rodents. This implant provides sustained release of the therapeutic agent during the treatment or prevention of the disorder of the eye. This implant configuration is particularly well-suited for placement in the sub-Tenon's space (also known as the bulbar sheath), but is not limited thereto and could be installed on or in other eye regions where convenient and useful.

The implants of this invention can be used to treat a number of eye diseases and indications including, for example, age-related macular degeneration, glaucoma, diabetic retinopathy, uveitis, retinopathy of prematurity in newborns, choroidal melanoma, chorodial metastasis, and retinal capillary hemangioma.

General Definitions

The following general definitions are supplied in order to facilitate the understanding of the present invention.

As used herein, the term "nutraceutical" refers to an isolated nutrient that may have therapeutic benefit against a disease or disorder. A non-limiting example of a nutraceutical oil is an omega-3 fish oil.

As used herein the term "radius of curvature" refers to the radius of a circle that best fits the curved surface at a given point.

As used herein, the term "permeation agent" refers to a molecule that increases the permeability of a therapeutic agent. An ophthalmic permeation agent increases the permeability of a therapeutic agent with respect to tissues of the eye.

As used herein, the term "impression body" refers to a body used to alter a surface of another body by pressure. The impression body may have one or more features that produce an impression having a specific shape such as a curvature for example.

As used herein, the term "depression" refers to a region of a surface which is lower with respect to the majority of the surface. More specifically, the present specification describes a depression in a mold body which represents a region with a lower surface than the remainder of the contact surface of the mold body.

As used herein the term "ophthalmic permeation agent" (also known as "transport facilitator") refers to a compound that increases the permeability of a therapeutic agent into the tissues of the eye. Methylsulfonylmethane is a non-limiting example of an ophthalmic permeation agent.

As used herein, the term "microperimetry" refers to a technique which is used to assess the visual function of a specific area of the retina and fovea. It provides a quantifiable way to measure the regression or progression of retinal visual function in the examined eye. A dot of light is projected onto the retina at a specific intensity and the patient is asked to confirm reception of the light. Changes in the stimulus intensity followed by the patient response, provides the means to assess the retinal visual function. Variations in microperimetry include dynamic perimetry, two color (red and blue) perimetry and static perimetry and are known to those skilled in the art.

As used herein, the term "multi-focal electroretinography" refers to a technique for determining the activity of retinal cells. When bioelectrical changes occur within the retina, the change is propagated to the surface of the cornea. These small (and often very fast) signals can be captured by an electrode placed on the surface of the cornea. The subject fixates on the center of a display containing an array of hexagons that increase in size from the center outward. Because the number of cone photoreceptors per area varies for different parts of the retina, the size of the hexagons is adjusted, so about the same number of cones will be stimulated by each hexagon. While the subject views the display, a single continuous electroretinogram recording is obtained.

As used herein, an "intraocular implant" refers to a device or element that is structured, sized, or otherwise configured to be placed in an eye. Intraocular implants are generally biocompatible with physiological conditions of an eye and do not cause adverse side effects. Intraocular implants may be placed in an eye without disrupting vision of the eye.

As used herein, a "therapeutic component" refers to a portion of an intraocular implant comprising one or more therapeutic agents or substances used to treat a medical condition of the eye.

As used herein, "associated with" means mixed with, dispersed within, coupled to, covering, or surrounding.

As used herein, an "ocular region" or "ocular site" refers generally to any area of the eyeball, including the anterior and posterior segment of the eye, and which generally includes, but is not limited to, any functional (e.g., for vision) or structural tissues found in the eyeball, or tissues or cellular layers that partly or completely line the interior or exterior of the eyeball. Specific examples of areas of the eyeball in an ocular region include the anterior chamber, the posterior chamber, the vitreous cavity, the choroid, the suprachoroidal space, the conjunctiva, the subconjunctival space, the episcleral space, the intracorneal space, the epicorneal space, the sclera, the pars plana, surgically-induced avascular regions, the macula, and the retina.

As used herein, an "ocular condition" is a disease, ailment or condition which affects or involves the eye or one of the parts or regions of the eye. Broadly speaking the eye includes the eyeball and the tissues and fluids which constitute the eyeball, the periocular muscles (such as the oblique and rectus muscles) and the portion of the optic nerve which is within or adjacent to the eyeball.

An "anterior ocular condition" is a disease, ailment or condition which affects or which involves an anterior (i.e. front of the eye) ocular region or site, such as a periocular muscle, an eye lid or an eye ball tissue or fluid which is located anterior to the posterior wall of the lens capsule or ciliary muscles. Thus, an anterior ocular condition primarily affects or involves the conjunctiva, the cornea, the anterior chamber, the iris, the posterior chamber (behind the retina but in front of the posterior wall of the lens capsule), the lens or the lens capsule and blood vessels and nerve which vascularize or innervate an anterior ocular region or site. Thus, an anterior ocular condition can include a disease, ailment or condition, such as for example, aphakia; pseudophakia; astigmatism; blepharospasm; cataract; conjunctival diseases; conjunctivitis; corneal diseases; corneal ulcer; dry eye syndromes; eyelid diseases; lacrimal apparatus diseases; lacrimal duct obstruction; myopia; presbyopia; pupil disorders; refractive disorders and strabismus. Glaucoma can also be considered to be an anterior ocular condition because a clinical goal of glaucoma treatment can be to reduce a hypertension of aqueous fluid in the anterior chamber of the eye (i.e. reduce intraocular pressure).

A "posterior ocular condition" is a disease, ailment or condition which primarily affects or involves a posterior ocular region or site such as choroid or sclera (in a position posterior to a plane through the posterior wall of the lens capsule), vitreous, vitreous chamber, retina, optic nerve (i.e. the optic disc), and blood vessels and nerves which vascularize or innervate a posterior ocular region or site. Thus, a posterior ocular condition can include a disease, ailment or condition, such as for example, acute macular neuroretinopathy; Behcet's disease; choroidal neovascularization; diabetic uveitis; histoplasmosis; infections, such as fungal or viral-caused infections; macular degeneration, such as acute macular degeneration, non-exudative age related macular degeneration and exudative age related macular degeneration; edema, such as macular edema, cystoid macular edema and diabetic macular edema; multifocal choroiditis; ocular trauma which affects a posterior ocular site or location; ocular tumors; retinal disorders, such as central retinal vein occlusion, diabetic retinopathy (including proliferative diabetic retinopathy), proliferative vitreoretinopathy (PVR), retinal arterial occlusive disease, retinal detachment, uveitic retinal disease; sympathetic opthalmia; Vogt Koyanagi-Harada (VKH) syndrome; uveal diffusion; a posterior ocular condition caused by or influenced by an ocular laser treatment; posterior ocular conditions caused by or influenced by a photodynamic therapy, photocoagulation, radiation retinopathy, epiretinal membrane disorders, branch retinal vein occlusion, anterior ischemic optic neuropathy, non-retinopathy diabetic retinal dysfunction, retinitis pigmentosa, and glaucoma. Glaucoma can be considered a posterior ocular condition because the therapeutic goal is to prevent the loss of or reduce the occurrence of loss of vision due to damage to or loss of retinal cells or optic nerve cells (i.e. neuroprotection).

The term "biodegradable polymer" refers to a polymer or polymers which degrade in vivo, and wherein degradation of the polymer or polymers over time occurs concurrent with or subsequent to release of the therapeutic agent. Specifically, hydrogels such as methylcellulose which act to release drug through polymer swelling are specifically excluded from the term "biodegradable polymer". The terms "biodegradable" and "bioerodible" are equivalent and are used interchangeably herein. A biodegradable polymer may be a homopolymer, a copolymer, or a polymer comprising more than two different polymeric units.

The term "treat", "treating", or "treatment" as used herein, refers to reduction or resolution or prevention of an ocular condition, ocular injury or damage, or to promote healing of injured or damaged ocular tissue.

The term "therapeutically effective amount" as used herein, refers to the level or amount of agent needed to treat an ocular condition, or reduce or prevent ocular injury or damage without causing significant negative or adverse side effects to the eye or a region of the eye.

A Two-Layer Ocular Implant for Treatment of Macular Degeneration

An example embodiment of the ocular implant of the present invention will now be described with reference to FIGS. 1 to 5. Skilled artisans will appreciate that elements in the figures are illustrated for simplicity and clarity and have not necessarily been drawn to scale. For example, the dimensions of some of the features shown in the figures may be enlarged relative to other elements to better illustrate and/or facilitate the discussion herein of the embodiments of the invention. Features in the various figures identified with the same reference numerals represent like features, unless indicated otherwise. Alternative features of alternative embodiments will also be discussed in context of the features of this example embodiment.

One embodiment of the present invention is a curved two-layer composite ocular implant. The curved shape of the implant 10 is indicated by dotted lines 12 and 14 in FIGS. 1 and 2. This shape may be formed by using a molding process which will be described in detail hereinbelow.

The ocular implant is formed of two curved layers, a lower layer 16 and an upper layer 18 as can be seen in the cross-sectional view of FIG. 3 which is taken along line 3'-3' of FIG. 2. In this particular embodiment, the lower layer 16 is formed of a silicone adhesive which contains a therapeutic agent 20. The two layers are demarcated by line 26 (FIG. 3). The lower layer 16 has a lower surface 24 which makes contact with the sclera E3 when the implant is in use.

A number of different therapeutic agents can be delivered to the eye by the ocular implant of the present invention. Such therapeutic agents include, but are not limited to: antibiotic agents such as fumagillin analogs, minocycline, fluoroquinolone, cephalosporin antibiotics, herbimycon A, tetracycline, chlortetracycline, bacitracin, neomycin, polymyxin, gramicidin, oxytetracycline, chloramphenicol, gentamicin and erythromycin; antibacterial agents such as sulfonamides, sulfacetamide, sulfamethizole, sulfoxazole, nitrofurazone, and sodium propionate; antiviral agents such as idoxuridine, famvir, trisodium phosphonoformate, trifluorothymidine, acyclovir, ganciclovir, DDI and AZT, protease and integrase inhibitors; anti-glaucoma agents such as beta blockers (timolol, betaxolol, atenolol), prostaglandin analogues, hypotensive lipids, and carbonic anhydrase inhibitors; antiallergenic agents such as antazoline, methapyriline, chlorpheniramine, pyrilamine and prophenpyridamine; anti-inflammatory agents such as hydrocortisone, leflunomide, dexamethasone phosphate, fluocinolone acetonide, medrysone, methylprednisolone, prednisolone phosphate, prednisolone acetate, fluoromethalone, betamethasone, triamcinolone acetonide, adrenalcortical steroids and their synthetic analogues, and 6-mannose phosphate; antifungal agents such as fluconazole, amphotericin B, liposomal amphotericin B, voriconazole, imidazole-based antifungals, tiazole antifungals, echinocandin-like lipopeptide antibiotics, lipid formulations of antifungals; polycations and polyanions such as suramine and protamine; decongestants such as phenylephrine, naphazoline, and tetrahydrazoline; anti-angiogenesis compounds including those that can be potential anti-choroidal neovascularization agents such as 2-methoxyestradiol and its analogues (e.g., 2-propynl-estradiol, 2-propenyl-estradiol, 2-ethoxy-6-oxime-estradiol, 2-hydroxyestrone, 4-methoxyestradiol), VEGF antagonists such as VEGF antibodies and VEGF antisense, angiostatic steroids (e.g., anecortave acetate and its analogues, 17-ethynylestradiol, norethynodrel, medroxyprogesterone, mestranol, androgens with angiostatic activity such as ethisterone), thymidine kinase inhibitors; adrenocortical steroids and their synthetic analogues including fluocinolone acetonide and triamcinolone acetonide and all angiostatic steroids; immunological response modifying agents such as cyclosporineA, Prograf (tacrolimus), macrolide immunosuppressants, mycophenolate mofetil, rapamycin, and muramyl dipeptide, and vaccines; anti-cancer agents such as 5-fluorouracil, platinum coordination complexes such as cisplatin and carboplatin, adriamycin, antimetabolites such as methotrexate, anthracycline antibiotics, antimitotic drugs such as paclitaxel and docetaxel, epipdophylltoxins such as etoposide, nitrosoureas including carmustine, alkylating agents including cyclophosphamide; arsenic trioxide; anastrozole; tamoxifen citrate; triptorelin pamoate; gemtuzumab ozogamicin; irinotecan hydrochloride; leuprolide acetate; bexarotene; exemestrane; epirubicin hydrochloride; ondansetron; temozolomide; topoteanhydrochloride; tamoxifen citrate; irinotecan hydrochloride; trastuzumab; valrubicin; gemcitabine HCL; goserelin acetate; capecitabine; aldesleukin; rituximab; oprelvekin; interferon alfa-2a; letrozole; toremifene citrate; mitoxantrone hydrochloride; irinotecan HeL; topotecan HCL; etoposide phosphate; gemcitabine HCL; and amifostine; antisense agents; antimycotic agents; miotic and anticholinesterase agents such as pilocarpine, eserine salicylate, carbachol, diisopropyl fluorophosphate, phospholine iodine, and demecarium bromide; mydriatic agents such as atropine sulfate, cyclopentane, homatropine, scopolamine, tropicamide, eucatropine, and hydroxyamphetamine; differentiation modulator agents; sympathomimetic agents such as epinephrine; anesthetic agents such as lidocaine and benzodiazepam; vasoconstrictive agents; vasodilatory agents; polypeptides and protein agents such as angiostatin, endostatin, matrix metalloproteinase inhibitors, platelet factor 4, interferon-gamma, insulin, growth hormones, insulin related growth factor, heat shock proteins, humanized antiIL2 receptor mAb (Daclizumab), etanercept, mono and polyclonal antibodies, cytokines, antibody to cytokines; neuroprotective agents such as calcium channel antagonists including nimodipine and diltiazem, neuroimmunophilin ligands, neurotropins, memantine and other NMDA antagonists, acetylcholinesterase inhibitors, estradiol and analogues, vitamin B12 analogues, alpha-tocopherol, NOS inhibitors, antioxidants (e.g. glutathione, superoxide dismutase), metals like cobalt and copper, neurotrophic receptors (Akt kinase), growth factors, nicotinamide (vitamin B3), alpha-tocopherol (vitamin E), succinic acid, dihydroxylipoic acid, fusidic acid; cell transport/mobility impending agents such as colchicine, vincristine, cytochalasin B; carbonic anhydrase inhibitor agents; integrin antagonists; lipophilic agents such as Idebenone, rapamycin, 2-cyano-3,12 dioxooleana-1,9 dien-28-imidazolide (CDDO-Im), 2-cyano-3,12-dioxooleana-1,9(11)-dien-28-oic acid-ethyl amide (CDDO-ethyl amide), and 2-cyano-3,12-dioxooleana-1,9(11)-dien-28-oic acid trifluoroethyl amide (CDDO-TFEA); and lubricating agents. Any of these therapeutic agents may be included in the ocular implant either singly or in combinations thereof.

This listing of therapeutic agents is illustrative, and not exhaustive. Other drugs that could be delivered by the ocular implant include, for example, thalidomide. Reference can be made to Remington's Pharmaceutical Sciences, Mack Publishing Press, Easton, Pa., U.S.A., to identify other possible therapeutic agents for the eye. Any pharmaceutically acceptable form of the agents can be used, such as the free base form or a pharmaceutically acceptable salt or ester thereof. In this particular embodiment, the dosage of the therapeutic agent provided by the implant is in the range of 1-100 mg, which is an appropriate dosage for a drug such as sulforaphane which is used in the treatment of macular degeneration.

The upper layer 18 is formed of a polymer which may be a silicone polymer or another polymer. Examples of polymers suitable for forming the upper layer 18 include, but are not limited to, polyvinyl acetate, cross-linked polyvinyl alcohol, cross-linked polyvinyl butyrate, ethylene ethylacrylate co-polymer, polyethyl hexylacrylate, polyvinyl chloride, polyvinyl acetals, plasiticized ethylene vinylacetate copolymer, polyvinyl alcohol, polyvinyl acetate, ethylene vinylchloride copolymer, polyvinyl esters, polyvinylbutyrate, polyvinylformal, polyamides, polymethylmethacrylate, polybutylmethacrylate, plasticized polyvinyl chloride, plasticized nylon, plasticized soft nylon, plasticized polyethylene terephthalate, natural rubber, polyisoprene, polyisobutylene, polybutadiene, polyethylene, polytetrafluoroethylene, polyvinylidene chloride, polyacrylonitrile, cross-linked polyvinylpyrrolidone, polytrifluorochloroethylene, chlorinated polyethylene, poly(1,4'-isopropylidene diphenylene carbonate), vinylidene chloride, acrylonitrile copolymer, vinyl chloride-diethyl fumarate copolymer, silicone rubbers, medical grade polydimethylsiloxanes, ethylene-propylene rubber, silicone-carbonate copolymers, vinylidene chloride-vinyl chloride copolymer, vinyl chloride-acrylonitrile copolymer or vinylidene chloride-acrylonitride copolymer or any suitable equivalent of these polymers or combinations thereof. In certain alternative embodiments, the polymer is a silicone adhesive which may be the same as the silicone adhesive used to form the lower layer 16.

As noted above, the lower layer 16 is formed of a medical grade silicone adhesive, generally is a polydimethylsiloxane (PDMS)-based compound. The silicone adhesive is biologically (physiologically) inert and is well tolerated by body tissues. Suitable silicones for use in the practice of this embodiment include MED-6810 silicone, MED1-4213, MED2-4213 silicone, which can be obtained from NuSil Technology LLC (Carpinteria, Calif., USA). Other biocompatible silicone adhesives may be used and can be adapted for use in preparation of implants according to certain alternative embodiments of the present invention. The time and temperature needed to cure the silicone will depend on the silicone used and the drug release profile desired. These silicones, if left to cure at room temperature (e.g., 20-30° C.) will require about 24 hours or more to cure. The cure rate will increase with increasing cure temperatures. For instance, MED2-4213 silicone will cure in about 30 minutes at about 100° C. As will be discussed in more detail below, the more quickly the silicone is cured, the less opportunity for therapeutic agent to leach out of the layer. In some cases, a catalyst such as platinum may be used to induce curing.

Figure 5:
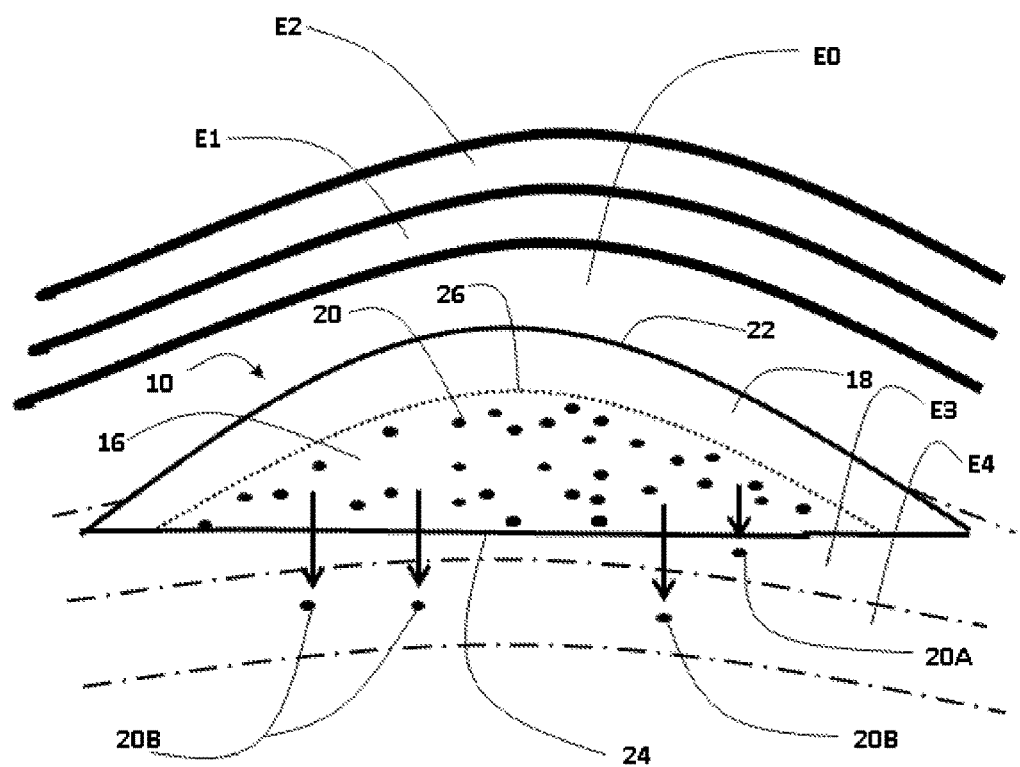
FIG. 5. A magnified view of the rectangular inset 5' of FIG. 4 showing a perspective view of the implant embodiment of FIGS. 1-4. Also shown are additional layers of structures and tissues within the eye and diffusion of a drug 20 to the sclera E3 and the choroid E4.

Dimensions of the ocular implant may vary. However, in this particular embodiment, the implant 10 has a diameter of 7 mm and a thickness of 2 mm. In this particular embodiment, each of the two layers 16 and 18 is 1 mm thick. In this particular embodiment, the upper surface 22 of the upper layer 18 has a radius of curvature of 5 mm for generally conforming to the radius of curvature of the surface of Tenon's capsule E1 of an average human eye (as indicated in FIG. 5). Likewise, the lower layer 16 is also curved with a similar radius of curvature configured to generally conform to the radius of curvature of the sclera E3 of an average human eye. These dimensions provide the implant 10 with characteristics appropriate for implantation with scleral contact in the sub-Tenon's space E0 of a human. It will be understood by the skilled person that these dimensions should be modified appropriately for an implant designed for use in an experimental animal such as a rat, mouse or rabbit for example. Armed with the knowledge of average dimensions of the eye and radii of curvature of Tenon's capsule and sclera of the chose experimental animal, the dimensions of an ocular implant according to may be selected by the skilled person and appropriate molding tools may be constructed without undue experimentation.

It is advantageous to provide the ocular implant with an upper layer 18 which is generally resistant to diffusion of the therapeutic agent 20 which is dispersed in the lower layer 16. In certain embodiments, the upper layer 18 is impermeable to the therapeutic agent 20. In other embodiments, the therapeutic agent 20 has a rate of diffusion within the upper layer 18 which is significantly less than the rate of diffusion of the therapeutic agent 20 out of the lower layer 16 and into the sclera. In this context, the term "significantly less" means 30%, 40%, 50%, 60%, 70%, 80%, 90% or 99% less than the rate of diffusion of the therapeutic agent 20 out of the lower layer 16 and into the sclera E3. The reduced diffusion characteristics of the therapeutic agent 20 in the upper layer 18 relative to the lower layer 16 provide the advantage of preventing loss of the therapeutic agent 20 to tissues where it is not needed. The reduced rate of diffusion of the therapeutic agent 20 through the upper layer 18 thereby encourages unidirectional diffusion of the therapeutic agent 20 from the lower layer 16 into the sclera E3 and choroid E4 for transfer to the macula E6 where its desired mechanism of action will be effected. A further advantage provided by the reduced diffusion characteristics of the therapeutic agent 20 in the upper layer 18 relative to the lower layer 16 is gained in preventing the therapeutic agent 20 from entering the lymphatic system via Tenon's capsule E1 and the conjunctiva E2 for transfer to other tissues where it may cause undesirable side-effects. Thus, in certain alternative embodiments of the present invention, the upper layer 18 or lower layer 16 further includes an agent that blocks lymphatic absorption.

In this particular embodiment, the thickness of the implant is 2 mm with the two layers 16 and 18 each being 1 mm in thick. The skilled person will appreciate that the thickness of each layer may be modified according to various embodiments of the invention, which may include variations with respect to the composition of silicone adhesive of the lower layer, the polymer of the upper layer, or the properties of drugs and/or formulations thereof used in the implant. The dimensional thickness may be modified appropriately by the skilled person without undue experimentation.

In this particular embodiment, the drug 20 in the lower layer 16 is an Nrf2 regulator such as sulforaphane, which is used in the treatment of macular degeneration. The drug is released over time as the drug particles 20 diffuse through the lower layer 16.

Positioning of the implant 10 with respect to the anatomical structures of an eye E is indicated in FIGS. 4 and 5. In FIG. 4, the features of the implant 10 are omitted for clarity. For convenient reference, the anatomical structures shown in FIGS. 4 and 5 include the sub-Tenon's space E0, Tenon's capsule E1 (also known as the bulbar sheath), the sclera E3, the choroid E4 (shown in FIG. 5 only), the optic nerve E5, the macula E6, the vitreous humor E7 and the upper and lower eyelids E8 and E9.

Referring now to FIG. 5 (which represents a magnification of the inset labeled 5' in FIG. 4) there is provided additional detail regarding the placement of the implant 10. The implant 10 is located in the sub-Tenon's space E0 with its lower surface 24 resting upon the surface of the sclera E3. It is also seen that the upper surface 22 of the implant 10 has a curvature which generally conforms to the curvature of the surface of Tenon's capsule E1. This feature provides the advantage of minimizing discomfort to the eye as a result of contact of Tenon's capsule E1 with upper edges of the implant 10. The curved upper surface 22 is smooth and does not have sharp edges which would otherwise cause irritations and/or damage to the tissues of Tenon's capsule and possibly also the conjunctiva E2 in the event that a sharp edge of an alternative implant were to completely puncture Tenon's capsule E1 and penetrate the conjunctiva E2.

Drug particles 20 will be released downward to the sclera E3 as indicated by the arrows in FIG. 5, because they are concentrated in the lower layer 16 and because the upper layer 18 is generally resistant to diffusion of the therapeutic agent 20 as described above. In FIG. 5, it is shown that three drug particles 20B have diffused from the lower layer 16 through the sclera E3 to the choroid E4 and one drug particle 20A has diffused from the lower layer 16 to the sclera E3. These drug particles 20A and 20B are expected to be transferred by either diffusion or an active physiological mechanism, or a combination thereof, to the macula E6 where the desired pharmaceutical effect will be obtained. Notably, FIG. 5 does not include arrows indicating diffusion of the therapeutic agent 20 into the upper layer 18 and to upper tissues in Tenon's capsule E1 and the conjunctiva E2. This is due to resistance of the upper layer 18 to diffusion of the therapeutic agent 20.

In certain embodiments, the implant 10 is provided with a suture platform (not shown) which can be formed as part of the implant to facilitate attachment of the implant 10 to the sclera E3. An implant having a suture platform with a mesh contained therein to hold sutures in place is described in U.S. Pat. No. 7,658,364 (which is incorporated herein by reference in entirety). The implant described herein can be modified without undue experimentation to include such a suture platform by modification of the molding processes which will be described in detail hereinbelow. Alternatively the implant of the invention may also be fixed to a suture stub as described also in U.S. Pat. No. 7,658,364.

A mold assembly comprising two impression bodies and molding process using this mold assembly for forming a two-layer ocular implant.

Figure 6:
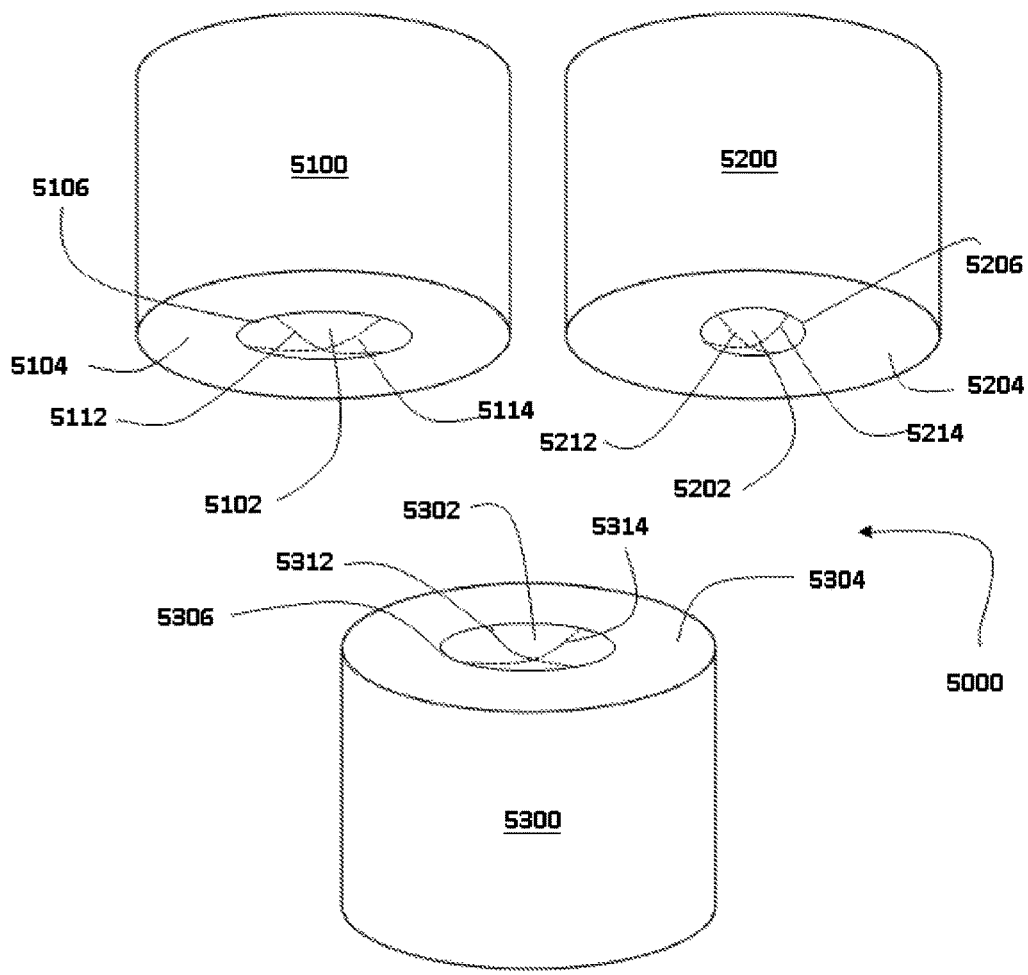
FIG. 6. A perspective view of an embodiment of a mold assembly for manual molding of an implant with features similar to those of the implant of FIGS. 1-5. This particular mold assembly 5000 includes two different impression bodies for forming inner curved surfaces of the two layers of the implant. The assembly includes a mold body 5300, a first impression body 5100 and a second impression body 5200. To more clearly show the protrusions 5102 and 5202 of the impression bodies 5100 and 5200, the upper ends of the impression bodies 5100 and 5200 are tilted in perspective backward into the plane of the page relative to the mold body 5300 to expose their contact surfaces.

In accordance with further aspects of the present invention, there is provided a mold assembly and molding process for forming a two-layer ocular implant. One particular embodiment of the mold assembly is shown in FIG. 6. This mold assembly embodiment is suitable for manual manipulation and may be adapted for automated use as well. This embodiment will be first described in terms of its structure and description of its manner of operation and will follow in context of FIGS. 7-9 wherein the reference numeral scheme is the same as that of FIG. 6.

The mold assembly of this particular embodiment is a three-piece mold assembly 5000 comprising a mold body 5300 which includes a depression 5302 in its upper contact surface 5304. The depression 5300 is provided with a downward curving inner surface as shown by dotted lines 5312 and 5314 (in the same manner as shown for implant 10 of FIG. 1). This curved inner surface 5302 provides the means for forming a curvature in the upper surface of the upper polymer layer of the implant as exemplified by surface 22 in FIGS. 1-3. The perimeter of the depression 5302 is shown at 5306.

Mold assembly 5000 also includes a first impression body 5100 which includes a protrusion 5102 on the mold contact surface 5104. The protrusion 5102 is downwardly curved as generally indicated by dotted lines 5112 and 5114. The perimeter of protrusion 5102 is shown as 5106 and in this particular embodiment, the perimeter 5106 of protrusion 5102 has a diameter similar to the diameter of the depression 5302 in mold body 5300. It is this curved protrusion 5102 that provides the means for forming a curvature in the boundary surface of the upper polymer layer of the implant as exemplified by surface 26 in FIGS. 1-3. The perimeter of the protrusion 5102 is shown at 5306.

The mold assembly 5000 also includes a second impression body 5200. This second impression body 5200 is generally similar to that of the first impression body 5100 with the exception that its protrusion 5202 has a smaller diameter as indicated at perimeter 5206 on contact surface 5204. In certain alternative embodiments, the radius of curvature of this protrusion 5202 is the same as the radius of curvature of the protrusion 5102 of impression body 5100. In the present embodiment, the curvature of protrusion 5202, as indicated by dotted lines 5212 and 5214 is different from that of protrusion 5102 of the first impression body 5100. It is this shallower protrusion 5202 that provides the means for forming a curvature in the lower surface of the lower silicone-drug layer of the implant as exemplified by surface 24 in the implant embodiment shown in FIGS. 1-3.

Notably, parts 5100, 5200 and 5300 are shown as cylinders in this embodiment. In this particular embodiment, this shape is selected to enable these parts to fit snugly into an appropriately dimensioned centrifuge tube for degassing of the materials used to form the implant, prior to initiation of the molding and/or the curing process. It is advantageous to ensure that the silicone adhesive is degassed prior to molding of the implant. This results in unhindered diffusion of the drug through the silicone, as air bubbles or pockets are eliminated which otherwise would not permit such diffusion. As a result, a controlled and predictable drug release rate can be obtained. In this embodiment, centrifugation is used to degas the silicone adhesive by adding the silicone adhesive containing the drug particles to a 50 mL assay tube and centrifuging this tube for 2 minutes at 1-4 k RPM. Alternative degassing techniques may include vacuum degassing techniques which can be adapted for the present invention without undue experimentation.

Figure 7:
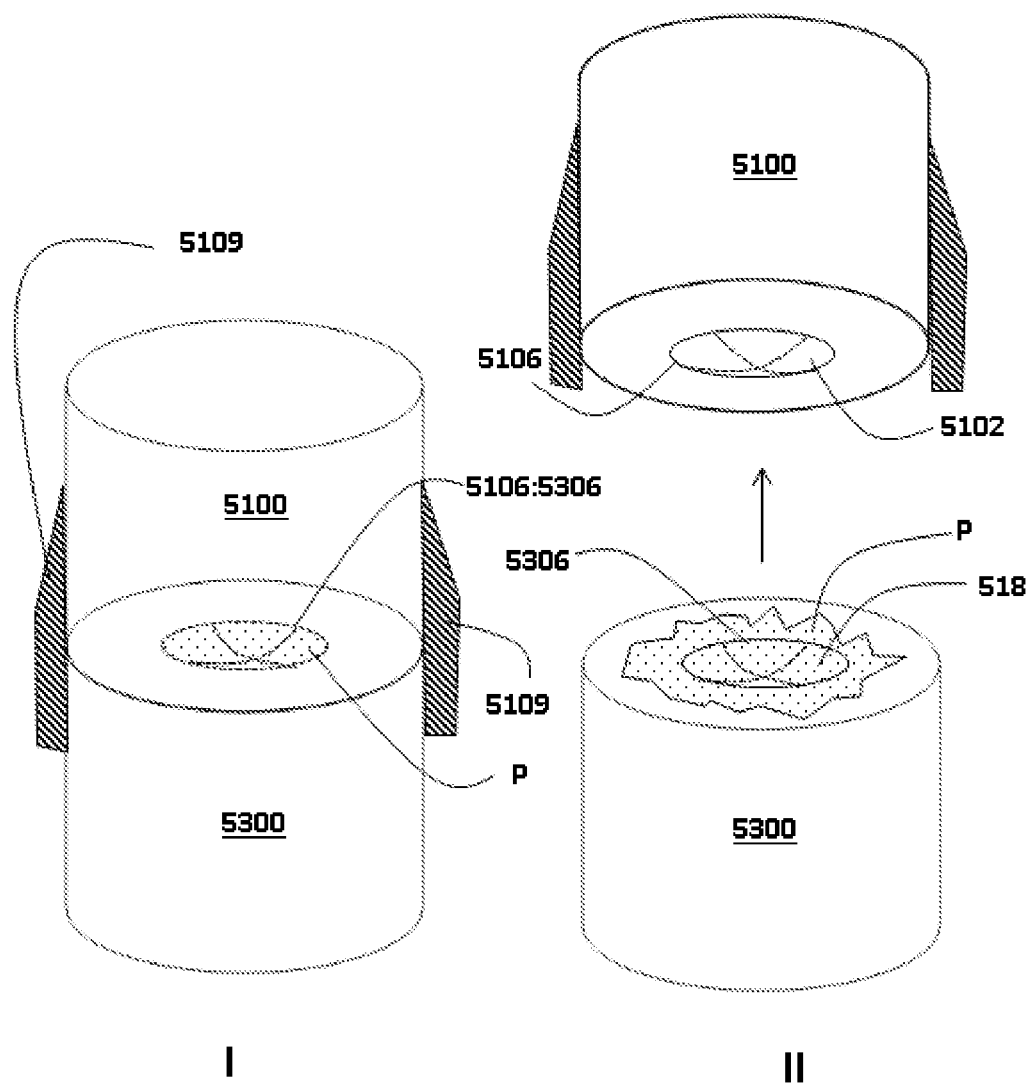
FIG. 7. A perspective view showing the fitting of the first impression body 5100 to mold body 5300 in a portion of the same embodiment of the mold assembly system (5000) shown in FIG. 6. Arrangement I (left side) depicts the assembled mold body 5300 and impression body 5100 with the perimeter of mold protrusion 5106 of impression body 5100 substantially aligned with the perimeter of the mold depression 5306 as indicated by the label 5106:5306 with polymer P disposed in the depression 5302. Arrangement II (right side) shows the surface of mold body 5300 after removal of impression body 5100 (which, for clarity, is shown in a tilted perspective backwards into the plane of the page relative to mold body 5300 as described for FIG. 7). Formation of polymer layer 518 is indicated.

FIG. 7 indicates the functionality of the mold body 5300 and the first impression body 5100 with respect to each other. It should be understood that the operation of the mold body 5300 and the second impression body 5200 with respect to each other will be generally similar. In FIG. 7, several reference numerals are omitted for clarity but the parts of the mold assembly shown in FIG. 7 should be understood as being the same as those referenced in FIG. 6. Polymer P is added to the depression 5302 of mold bottom 5300 as indicated by the stippled arrow. Optionally, the mold body 5300 containing the polymer in depression 5302 may then be placed in a centrifuge tube and subjected to centrifugation to degas the polymer prior to molding and curing (as described above). Then, the first impression body 5100 is fitted to mold body 5300 such that surface 5104 makes contact with surface 5304 and the perimeter 5106 of the protrusion 5102 is substantially aligned with the perimeter 5306 of the depression 5302 of the mold body 5300 (as indicated in Arrangement I on the left side of FIG. 7). The alignment of perimeters 5306 and 5106 is indicated by the dotted line labeled 5106:5306 in FIG. 7. When the upper polymer layer 518 of the implant 510 (see FIG. 8) has been formed by the mold body 5300 and the first impression body 5100, the first impression body 5100 is removed (as shown in Arrangement II shown on the right side of FIG. 7). It is now seen that excess polymer P covers some of the top surface of mold body 5300. This excess polymer P may be trimmed away at this stage to facilitate tight fitting of the second impression body 5200 which is indicated in more detail in FIG. 8. An optional device for trimming excess materials is described hereinbelow. At this stage, the upper polymer layer 518 has been formed and the curing process may be initiated. The curing process may be initiated with the first impression body 5100 in place—to provide some hardness to the polymer layer. Alternatively, curing may be initiated before the impression body 5100 is fitted to the mold body 5300. In other alternative embodiments, the curing process is completed while the impression body 5100 remains fitted to the mold body 5300.

Shown in FIG. 7 (and omitted in FIGS. 6 and 8 for clarity) is a guide set comprising a pair of rails 5109 fixed to the first impression body 5100. This guide set provides the means for conveniently aligning the impression body 5100 with mold body 5300. It should be understood that this feature is optional and, although not shown as such in these figures, may also be provided on the second impression body 5200 or on any molding parts provided in alternative embodiments of the mold assembly of the present invention. Such a guide set may comprise more than two rails and the guide set may be formed integrally with the impression body part instead of being a separate part attached thereto.

Figure 8:
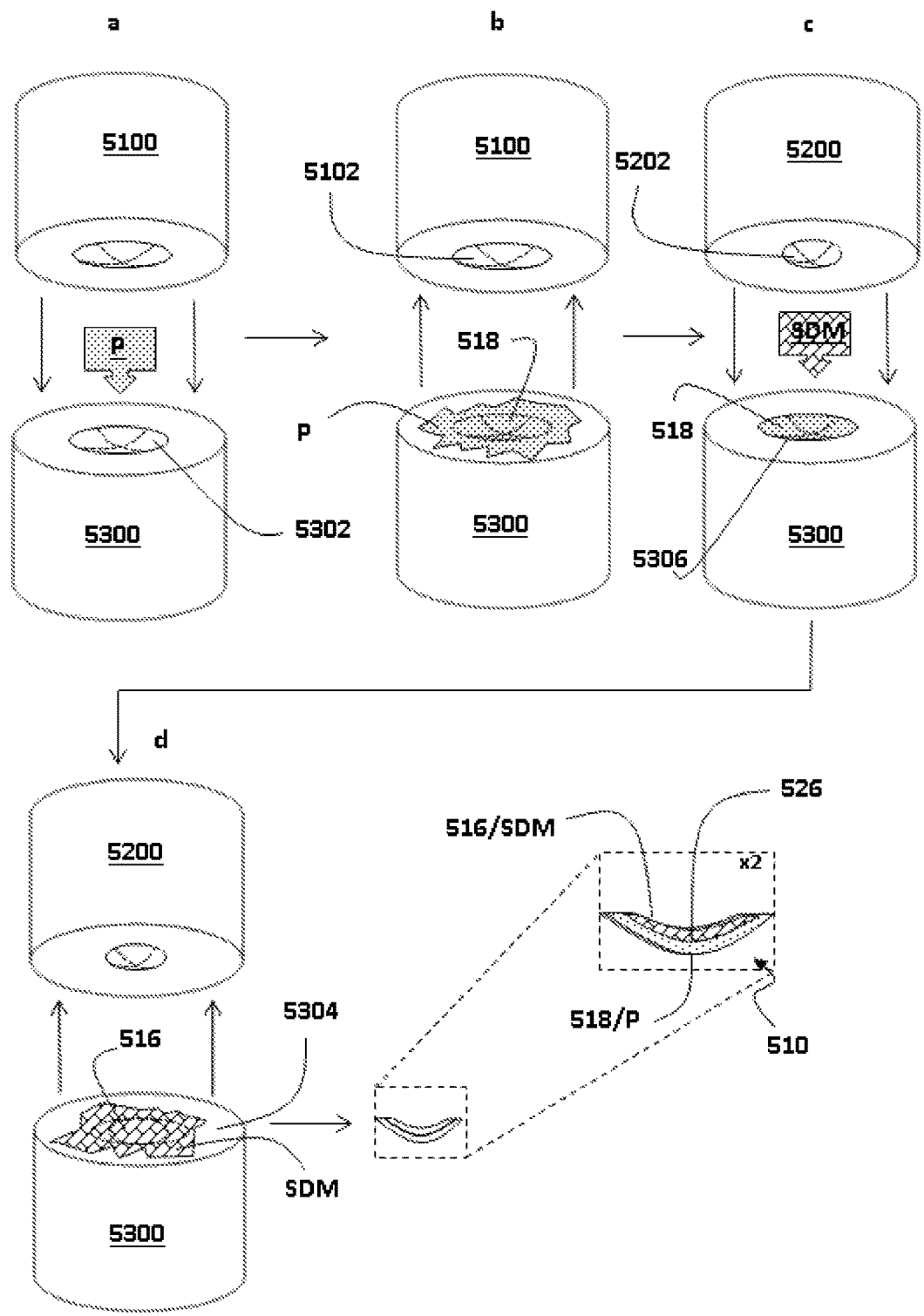
FIG. 8. A perspective view/process diagram showing the sequential fitting of mold assembly parts 5300, 5100 and 5200 of the mold assembly system embodiment of FIGS. 6 and 7 (5000) and provision of polymer P (stippled fill) and a silicone-drug mixture SDM (diagonal brick fill) in the process of molding an implant 510 comprising an upper polymer layer 518 and a lower layer 516 comprising a silicone-drug mixture. In all representations, impression bodies 5100 and 5200 are tilted in perspective relative to mold body 5300 as described in FIGS. 6 and 7.

FIG. 8 shows a process which uses the same mold assembly 5000 of FIGS. 6 and 7 for constructing a two-layer implant 510. In step a, polymer P is added to depression 5302 of mold body 5300 and the first impression body 5100 is fitted thereto as shown on the left side of FIG. 7.

When the first impression body 5100 is removed from mold body 5300, as shown in step b, it is seen that the polymer has been molded in the form of the upper polymer layer 518 and that excess polymer P covers some of the top surface of mold body 5300 (as also shown in FIG. 7). This excess polymer is trimmed at the perimeter 5306 of the depression 5302 such that only the polymer layer 518 remains. In alternative embodiments, it may be possible to avoid trimming at this stage if the excess polymer P does not interfere with subsequent molding steps which are described below.

This polymer layer 518 in its present orientation within the depression 5302 is defined by a lower downward curvature formed by depression 5302 and upper downward curvature formed by the molding action of the protrusion 5102 of the first impression body 5100. The curing process may be initiated and/or accelerated at this stage (not shown). The curing process may be begun with the first impression body 5100 in place, in order to provide some hardness to the polymer layer. Alternatively, curing may be initiated before the mold is in place. In other alternative embodiments, the curing process is taken to completion while the impression body 5100 remains fitted to the mold body 5300.

In step c, the silicone-drug mixture SDM is added to the polymer layer 518 which remains within depression 5302 of mold body 5300. It is advantageous at this stage to ensure that the polymer layer 518 is essentially completely cured in order to avoid mixing of the silicone-drug mixture SDM with the polymer P. It is also advantageous to conduct another degassing procedure at this stage. The mold body 5300 is placed in a centrifuge tube and centrifuged for 2 minutes at 1-4 k RPM to remove gas bubbles and ensure consistent diffusion of the drug through the silicone adhesive layer (as described above). Once the degassing procedure is complete, the second impression body 5200 is fitted to mold body 5300. In another embodiment, the degassing procedure is conducted while the mold assembly of parts 5300 and 5100 is assembled and also when the mold assembly of parts 5300 and 5100 is assembled. In this particular embodiment, the protrusion 5202 has dimensions different from the protrusion 5102 of the first impression body 5100 because a significant portion of the volume of depression 5302 is occupied by the cured (or curing) polymer layer 518 and it is not desirable to compress the polymer layer 518 as compression may cause damage. The fitting of the second impression body 5200 to the mold body 5300 places the perimeter of the protrusion 5202 of the second impression body 5200 substantially centrally within the perimeter of the depression 5302 of the mold body 5300. The curvature of the interface 526 (see inset of FIG. 8) between the polymer layer 518 and the silicone-drug layer 516 is formed by the hardened surface of the cured polymer layer 518 (which has the effect of acting as a mold surface). The downwardly curving upper surface of the silicone-drug layer 516 (as oriented in the inset of FIG. 8) is formed by the protrusion 5202 of the second impression body 5200.

As shown in step d, when the second impression body 5200 is removed from the mold body 5300, it is seen that excess silicone-drug mixture SDM covers part of the upper contact surface 5304 of the mold body 5300. This excess silicone-drug mixture SDM is then trimmed away. In certain embodiments, this trimming may optionally be performed using an appropriately dimensioned punching device (not shown) which is configured to cut a consistent circular shape through cured or partially cured layers 516 and 518. It may be advantageous to also use this punching device to remove the excess polymer P in step b as noted above. Advantageously, the punching device is coated with a material that enables cutting through cured layers 516 and 518 but does not cause damage to the upper contact surface 5304 which is preferably coated with Teflon® (polytetrafluoroethylene), aluminum or other material that facilitates removal of the molded implant 510 from the mold body 5300. Teflon is durable with respect to the temperatures required for curing the silicone, which is generally about 150° C., and after curing, the implant complex can be peeled off of the mold completely and the mold can be reused.

The final product of this process is the molded two-layer implant 510 which is shown in the inset of FIG. 8.

Figure 9:
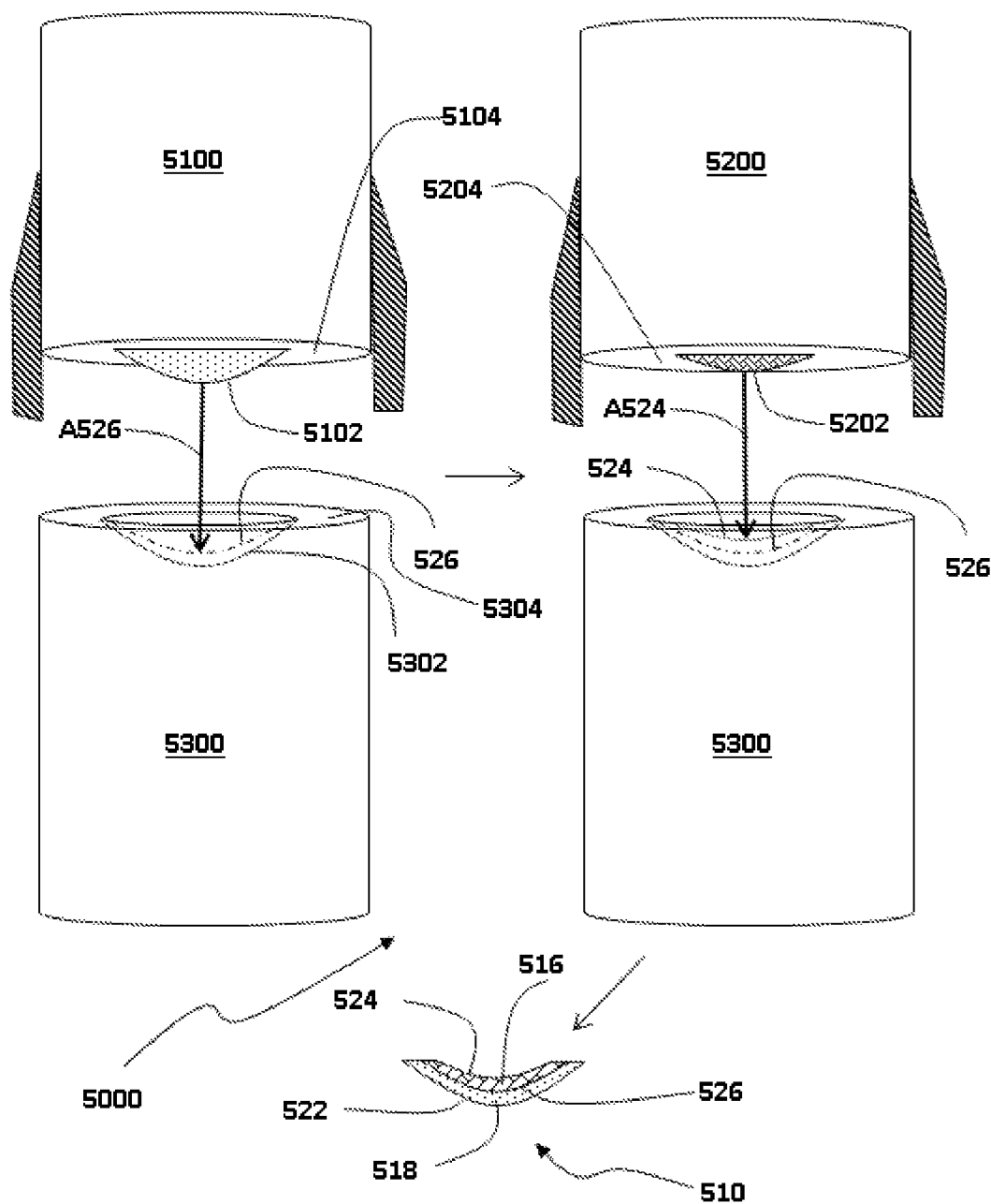
FIG. 9. A perspective view/process diagram showing the sequential fitting of mold assembly parts 5300, 5100 and 5200 of the mold assembly system embodiment of FIGS. 6-8 (5000) in sequential formation of the surfaces 526 and 524 of the implant 510. It is seen that the depth dimensions of the depression 5302 and the protrusions 5102 and 5202 determine the thickness of the layers 518 and 516 of the implant 510.

FIG. 9 shows perspective diagrams of the mold assembly system 5000 (as discussed above) to indicate more clearly how the curved interface surface 526 and the sclera-contacting surface 524 of the implant 510 are formed by the system 5000. Arrows A526 and A524 indicate the extent of travel of the protrusions 5102 and 5202, respectively. It is this extent of travel which defines the thickness of each of the layers 518 and 516 and which indicate how the surfaces 526 and 524 of the implant 510 are sequentially formed by the protrusions 5102 and 5202. The downward travel of the protrusion 5102 is halted when the contact surface 5104 of the first impression body 5100 encounters the contact surface 5304 of the mold body 5300. Likewise, the downward travel of the protrusion 5202 is halted when the contact surface 5204 of the first impression body 5200 encounters the contact surface 5304 of the mold body 5300. The dimensions of the protrusions 5102 and 5202 therefore are selected in conjunction with the depth of the depression 5302 of the mold body 5300 and the position of the formed interface surface 526 to provide layers 518 and 516 of the implant 510 with predetermined thicknesses. In one embodiment, the depression 5302 and protrusion 5102 cooperate to mold a polymer layer 518 with a thickness of 1 mm because the space between the surface of the depression 5302 and the protrusion 5102 is 1 mm when the surfaces 5304 and 5104 are in contact with each other. The upper surface 526 (in the orientation shown in FIG. 9) of the polymer layer 518 then cooperates with the protrusion 5202 of the second impression body 5202 to mold a silicone-drug layer 516 with a thickness of 1 mm because the space between surface 526 and protrusion 5202 is also 1 mm. Therefore, the thickness of the entire implant 510 of this embodiment is 2 mm. The upper surface 524 (in the orientation shown in FIG. 9) is also curved and configured to contact the sclera as shown in FIG. 5. The skilled person will recognize that changing the dimensions of the depression, 5302, and/or the protrusion 5102 and/or the protrusion 5202 will lead to production of implants with layers 516 and/or 518 of varying thicknesses and with varying radii of curvature. Therefore, any desired goal of thickness and radius of curvature of layers of the implants according to various embodiments of the invention may be obtained without undue experimentation.

The materials used to form the mold body parts 5300, 5100 and 5200 may vary. Advantageously, they are formed by injection molding of plastics or by 3D printing methods (additive manufacturing) and have contact surfaces 5304, 5104 and 5204 coated with Teflon®, aluminum or other non-stick material as noted above. The materials and coatings and optional compatible punching devices may be designed, constructed and tested by the skilled person without undue experimentation.

The properties of the polymer layer 518 and the silicone-drug layer 516 may be altered for maximum benefit by selection of an appropriate polymer for the polymer layer 518 and by altering curing processes. The extent of curing of layers 516 and 518 is expected to have an effect on the rate of diffusion of a given drug through that layer. Curing may be conducted over various lengths of time at room temperature or at temperatures as high as 50° C. for either or both of the layers 516 and 518. Experiments conducted to optimize the properties of the layers 516 and 518 can be performed routinely by the skilled person. Catalysts such as peroxide or platinum or photo-initiators such as LEDs may also be used to fine-tune the curing process. Other catalysts and photo-initiators for curing of biocompatible silicone adhesives are known in the art and can be selected for use with aspects of the present invention without undue experimentation.

In an alternative embodiment, the protrusions 5102 and/or 5202 may be provided by separate parts which can be alternatively connected to a single impression body part by a common coupling system such as a press-fit mechanism (not shown). Such an alternative mechanism may be designed and formed in plastic molded parts without undue experimentation.

While the embodiment of the mold assembly described in this section has two impression bodies 5100 and 5200 it may be possible in alternative embodiments, to dispense with the second impression body part 5200 in cases where the initially formed and cured polymer layer 518 is of sufficient flexibility that compression by the first impression body 5100 can be used to form the sclera-contacting curvature of the silicone-drug layer 516 without damage to the cured polymer layer 518. Such an alternative embodiment is described hereinbelow.

Figure 10:
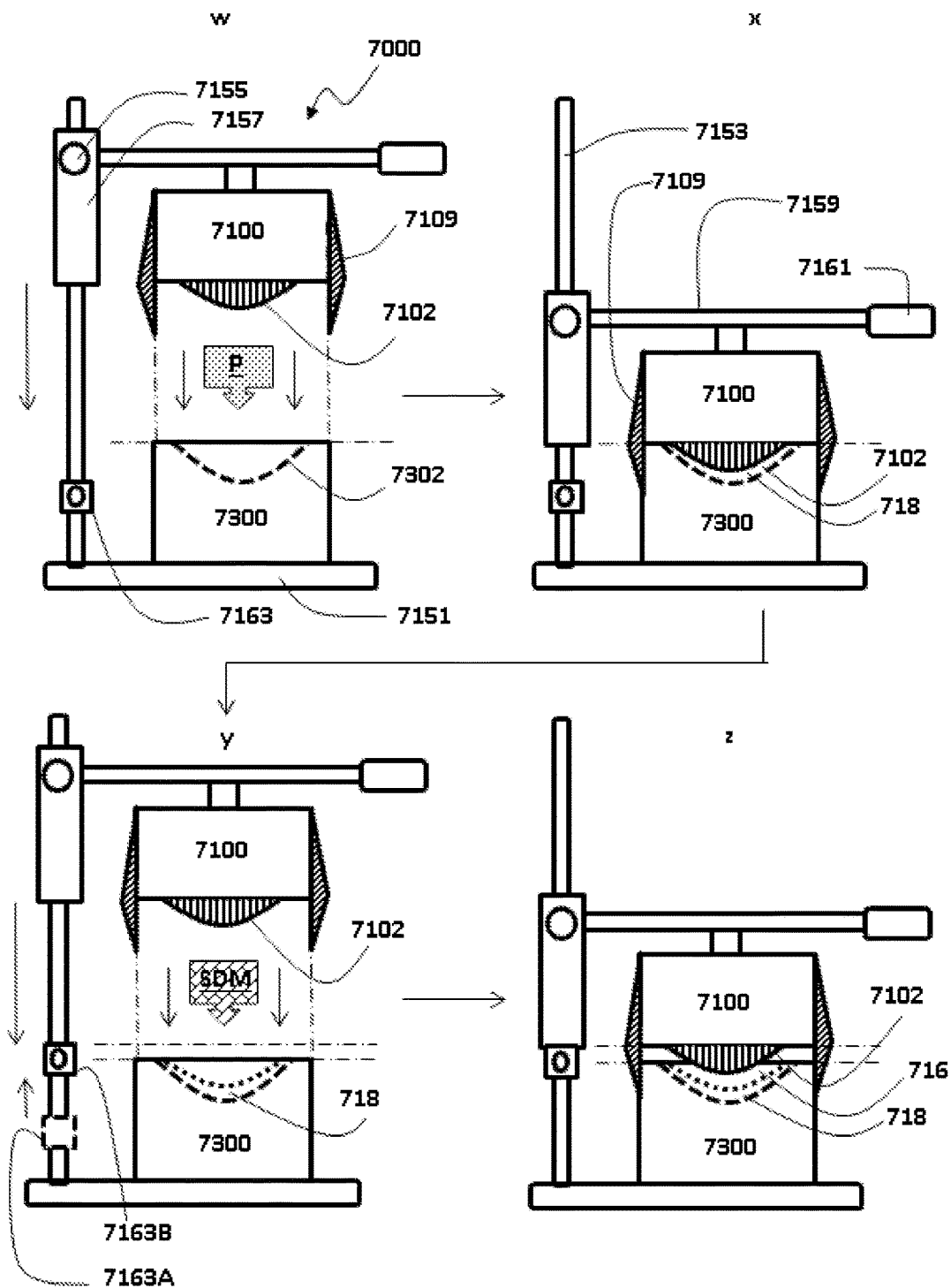
FIG. 10. A side view/process diagram showing the operation of a different embodiment of the mold assembly system 7000 where a single impression body 7100 is used to form both inner surfaces of the two layer implant as indicated in steps w, x, y and z. This embodiment includes a support frame that provides for vertical sliding movement (and locking) of the single impression body 7100 with respect to the fixed mold body 7300.

A mold assembly comprising a single impression body with a support frame and a molding process employing this mold assembly for forming a two-layer ocular implant In accordance with an additional aspect of the present invention, there is provided an additional mold assembly embodiment shown in FIG. 10. This mold assembly 7000 includes only a single impression body 7100 (in contrast to the other mold assembly embodiment described above which includes two mold impression bodies, each configured to form curvature in different surfaces). This particular mold assembly 7000 is provided with a support frame that enables slidable motion of the impression body 7100 with respect to the fixed mold body 7300 and locking of the impression body 7100 at predetermined positions for formation of two different curved surfaces in the two-layer implant—the interface surface as exemplified by surface 26 in FIG. 3 and the sclera-contacting surface of the silicone-drug layer of the implant as exemplified by surface 24 in FIG. 3.

This mold assembly 7000 includes a support frame which includes a base 7151 to which is attached a vertical support member 7153 equipped with a vertically slidable sleeve 7157. Sleeve 7157 has a locking mechanism 7155 provided by a screw clamp or other such locking arrangement which serves to halt the motion of the sleeve 7157 with respect to the vertical support member 7153. A horizontal arm 7159 is fixed to sleeve 7157 and includes an optional handle 7161 that can be gripped by a user to assist in effecting vertical movement of the arm 7159 by sliding of the sleeve 7157 over the vertical support member 7153. The vertical support member 7153 is also provided with a vertically slidable and lockable block 7163 which will prevent further vertical downward movement of the impression body when it is disposed at any location above the upper surface of mold body 7300.

Impression body 7100 is fixed to the lower surface of the arm 7159 and includes guide rails 7109 to ensure alignment of impression body 7100 with mold body 7300 which is fixed to the base 7151. Impression body 7100 is provided with a protrusion 7102 which is used to form two of the curved surfaces of the two-layer implant.

The outline of the mold body depression is shown with a dashed line at 7302. It is this depression that forms the upper curved surface of the polymer layer as exemplified by surface 22 in FIG. 3.

The four steps of this process are indicated as steps w, x, y and z in FIG. 10. In step w (upper left), impression body 7100 is first locked in place above the mold body 7300 and then polymer P is added to the depression 7302. Then impression body 7100 is unlocked and lowered by vertical downward movement of arm 7159. Impression body 7100 then stops when it encounters the upper surface of the mold body 7300 as shown in step x (upper right). In this manner, the polymer occupying the depression 7302 is formed with two curved surfaces into a polymer layer whose location is indicated at 718. This polymer layer is then cured according to processes described hereinabove.

Prior to step y (lower left), impression body 7100 is raised and locked into place by the locking mechanism 7155. The block 7163 is then moved from its original position at 7163A to a higher position indicated at 7163B and locked into place via its screw clamp mechanism. Then a silicone-drug mixture SDM is added to the exposed curved surface of the polymer layer which resides within the depression 7302 of mold body 7300. The locking mechanism 7155 is then disengaged and the impression body 7100 is lowered until the lower end of the sleeve 7157 encounters the upper end of the block 7163 (at position 7163B). At this position, the block 7163 prevents further downward movement of the impression body 7100. The result of this action is shown at step z (lower right) where it is seen that the protrusion 7102 of impression body 7100 is halted in its downward movement and forms a curved surface in the silicone-drug mixture residing on top of the polymer layer indicated at 718. The formation of this curved surface defines the shape of the silicone-drug layer as indicated at 716. The impression body 7100 may then be raised and locked into place on the vertical support member 7153.

After appropriate curing of the silicone-drug layer 716, the finished two-layer implant (not shown) may then be removed from the mold assembly 7000.

The skilled person will recognize that this mold assembly 7000 provides the means for preparing two-layer ocular implants with variations in the dimensions of the layers 716 and 718 according to the placement of the protrusion 7102 of the impression body 7100 which is provided by the movement and locking mechanisms of the sleeve 7157 and the block 7163 provided on the vertical support member 7155. It is expected to be advantageous to provide markings in the vertical support to indicate positions for the block 7163 to provide layers of predetermined thickness (not shown). The positions of these markings can be determined by the skilled person without undue experimentation.

The skilled person will also appreciate that this mold assembly can be modified in alternative embodiments to replace protrusion 7102 with a second protrusion of different dimensions, if needed. This can be done if protrusion 7102 is a removable part (with a snap-fit mechanism) rather than being integrally formed with the impression body. Alternatively, the entire impression body 7100 may be removed from the system 7000 and replaced with a different impression body (not shown) that has a protrusion with different dimensions than that of protrusion 7102.

These assemblies and methods for preparing the implant of this invention provide a two-layer implant having a controlled thickness of degassed silicone with no significant variability in the thickness in the layer, provided the method steps remain consistent. Also, rigorous post-production quality control inspections (including measuring individual implant release rates before in vivo use) of the implant products are not necessary. This reduces the chances for contamination of the device from additional handling as well as the cost of making the devices.

Kit for Production of Two-Layer Ocular Implants

The present invention also contemplates a kit for production of two-layer ocular implants. The kit may include any or all of the components and features thereof which are described above with reference to FIGS. 6-9. In a very basic embodiment, the kit includes a) a mold body with a depression on its contact surface; and b) an impression body with a protrusion on its contact surface configured to form a polymer layer with curved upper and lower surfaces and to also form a silicone-drug layer with curved upper and lower surfaces. This particular embodiment is used in conjunction with polymer and silicone adhesive materials provided separately which yield resilient cured layers that are resistant to damage by pressure of the upper mold body part against both layers.

An alternative embodiment of the kit further includes c) a second impression body with a protrusion on its contact surface which is configured to form the sclera-contacting surface of the silicone-drug layer.

An alternative embodiment of the kit further includes d) polymer and silicone materials for forming the layers of the two-layer ocular implant.

In some embodiments of the kit, the mold assembly body parts are cylindrical and the kit further includes e) centrifuge tubes for conducting degassing procedures.

In a further embodiment, the kit further includes a means for trimming the excess polymer and silicone from the contact surface of the mold body. In certain embodiments, this means for trimming is provided by a punching device dimensioned to consistently cut the perimeter of a two layer implant to specific dimensions.

In some embodiments, the kit includes instructions for using the components of the kit in a molding process for molding a two-layer ocular implant.

System and Process for Automated Mass Production of Ocular Implants

The present invention also contemplates a system for automated production of silicone ocular implants. An example embodiment and operation thereof will be described and possible modifications of various features will also be discussed in context of the features of this example embodiment. In this example embodiment, shown in FIG. 11, there is provided a system 1000 which includes an injection molding apparatus 1200 for automated production of implants 110. In alternative embodiments, the injection molding apparatus may be substituted for a different apparatus such as a 3D printer which is compatible with the components used in the construction of the implant and capable of additive manufacturing of two-layer ocular implants.

The injection molding apparatus 1200 is controlled by a computer at workstation 1300, which is also networked to either a local database 1400 or an internet database 1500. Database 1400 or 1500 contains information about ocular therapeutic agents such as their compatibility with various silicone adhesives and polymers and their rates of diffusion through the silicone adhesives and polymers. The database may also contain information about additives such as ophthalmic permeation agents, excipients, and agents that block lymphatic absorption. The database may also contain information regarding the curing processes for different silicone adhesives and polymers, including heating parameters, catalysts and photo-initiators.

Figure 11:
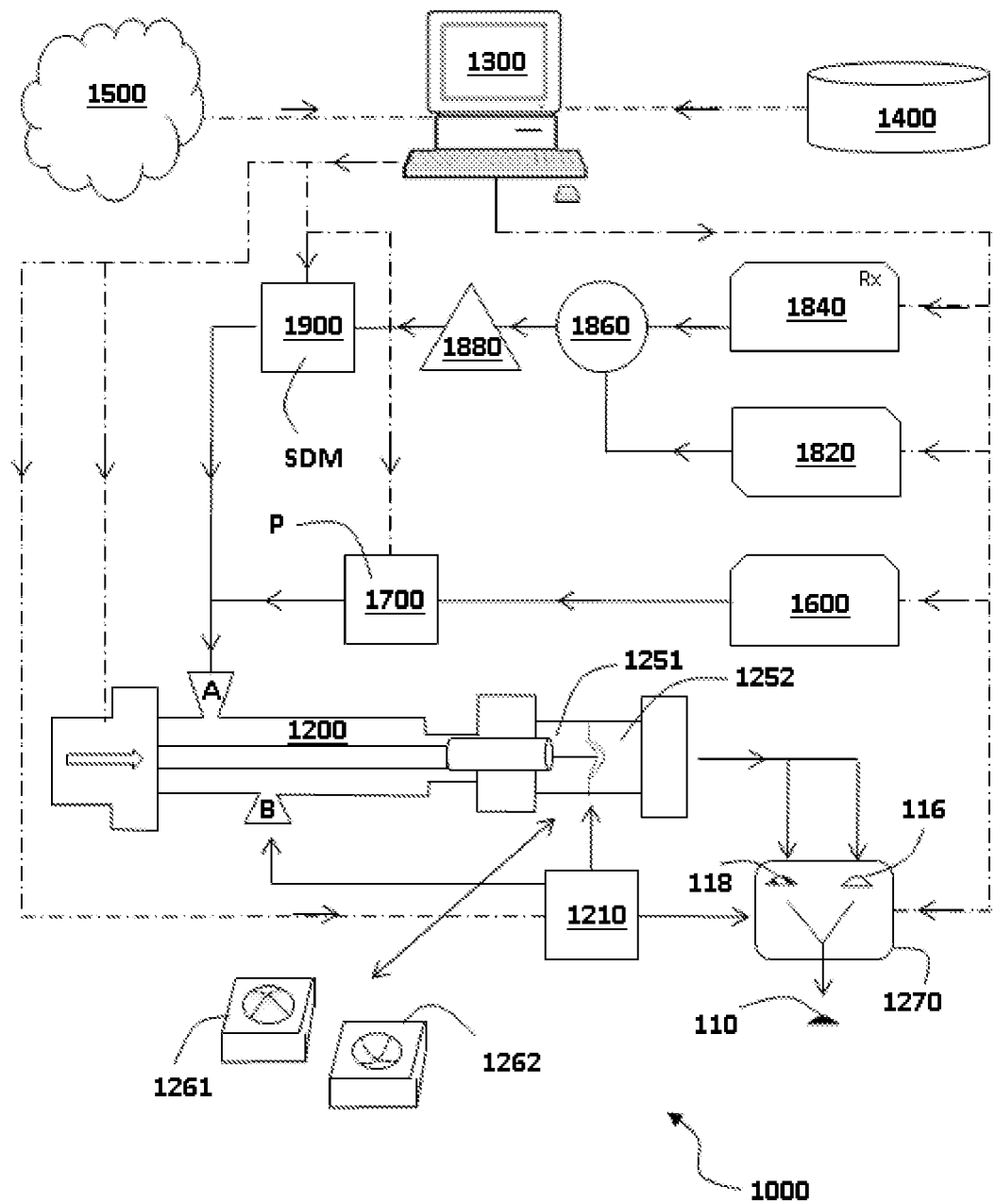
FIG. 11. A schematic diagram of a system 1000 for automatic production of an implant 110 according to one aspect of the present invention wherein the layers 160 and 180 of the implant 110 are formed separately by an injection molding apparatus 1200 and joined together by a layer assembly module 1270.

In FIG. 11, the dot-dashed lines represent data communication conduits (which may be provided by wires or by wireless communication) between the workstation 1300 and individual modules and the solid lines represent conduits for handling of materials used in construction of the implants 110. Movement of materials may be effected by robotic means or manually or by a combination thereof. The skilled person will understand that alternative embodiments are possible wherein one or more of the automatic tasks involving data and/or liquid handling communication may be overridden and performed manually by a user of the system.

The materials used to make the implants may be stored in individual libraries contained in the laboratory or production plant. In this particular embodiment, the libraries include a therapeutic agent library 1840, a silicone adhesive library 1820 and a polymer library 1600. A user can access the database 1400 or 1500 to determine compatibility of a given therapeutic agent in the library 1840 with respect to silicone adhesives contained in library 1820 and polymers contained in library 1600. Alternatively, the user may select a therapeutic agent from the therapeutic agent library 1840 and this action will automatically initiate an algorithm stored on the workstation 1300 or accessible via the internet, which will automatically identify appropriate silicone adhesives and polymers that will be compatible with the production of the two-layer implants 110 and enable a selection to be made.

The algorithm may further access the inventory of each of the libraries 1600, 1820 and 1840 to determine if the desired set of components is available in the laboratory or production plant and then provide this information to the user who may then elect to proceed with the currently selected production run or elect to choose alternative materials. This type of algorithm may be developed without undue experimentation by the skilled person.

Once a production run is initiated by a user, the algorithm provides instructions to select a silicone adhesive from silicone adhesive library 1820 and send it to a mixing apparatus 1860. In a similar manner, the algorithm provides instructions to select a therapeutic agent from the therapeutic agent library 1840 and send it to the mixing apparatus 1860 and also provides instructions to select a polymer from the polymer library 1600. The transfer of these and other components to various locations within the system 1000 may be effected by commercially available robotic liquid handlers, or may be effected by manual transfer. Solid particles containing the therapeutic agent may also be dispensed by robotic handlers configured to dispense powders or particles. Programming of such robotic handlers for tasks performed by the present embodiment of the system is a routine task for the person with ordinary skill.

Mixing of the therapeutic agent and the silicone adhesive is performed in a mixing apparatus 1860. One example of such a mixer is the SpeedMixer™ dual asymmetric centrifugal laboratory mixer (FlaxTek Inc., Landrum, S.C., USA). The mixture is then transferred to a degassing module 1880 which in certain embodiments is provided by a centrifuge as described above. The degassing process is performed to remove air bubbles from the silicone adhesive to ensure consistent diffusion rates of the therapeutic agent through the silicone adhesive. When the mixed and degassed silicone adhesive-drug mixture and the polymer are ready for further downstream processing, they are then transferred to their respective holding containers 1900 and 1700.

In this particular embodiment, the polymer layer 118 of the implant 110 is the first layer selected for molding. Instructions are transmitted from the workstation 1300 to the robotic system to effect transfer of the polymer P from the polymer holding container 1700 to the injection molding apparatus 1200 at port A where the polymer P is injected into the mold formed by mold plates 1251 and 1252 associated with the injection molding system 1200. If curing is to be accelerated, an optional curing module 1210 may be included in the system 1000. The curing module 1210 may be simply a light source for photo-initiation of curing at the mold portion 1251 and 1252 of the injection molding apparatus 1200 or may be provided by a container containing a liquid curing catalyst and a liquid handler configured to transfer the liquid curing catalyst to the injection molding apparatus 1200 at port B for transfer to the mold plates 1251 and 1252. The curing module 1210 may also cure one or both of the layers 116 and 118 while they reside within a layer assembly module 1270 which will be described in more detail hereinbelow. The curing module 1210 may also be under computer control at the workstation 1300.

In this particular embodiment, when the molding and curing of the polymer layer of a series of implants 110 is complete, the cured polymer layer 118 is removed from the mold plates 1251 and 1252. The system 1000 is then prepared for the molding of the silicone adhesive layer 116 from the silicone-drug mixture SDM. In one embodiment, the mold plates 1251 and 1252 are removed and replaced with new mold plates, shown generally as parts 1261 and 1262 which are configured to form the silicone adhesive layer 116. This process of replacing the mold plates 1251 and 1252 with mold places 1261 and 1262 (as indicated by the double arrow in FIG. 10) may be performed manually or by a robot (not shown). After the mold plates 1261 and 1262 are in place, the process of forming the silicone adhesive layer 116 may then begin. The silicone—drug mixture SDM (which may also contain other additives such as ophthalmic permeation agents or agents that block lymphatic absorption of the drug) in holding container 1900 is transferred to the injection molding apparatus 1200 at port A. This material is injected into the mold plates 1261 and 1262 and the silicone adhesive layer 116 is formed and cured, if necessary, by the curing module 1210.

In an alternative embodiment, another injection molding apparatus (not shown) may be provided for molding of the silicone adhesive layer 116 instead of substituting mold plates 1251 and 1252 for mold plates 1261 and 1262. While this embodiment would be more expensive, it would allow for more constant production by avoiding the need to clean the injection system and change the mold plates.

At this point, the system has produced a silicone adhesive layer 116 containing the therapeutic agent and a polymer layer 118 in separate production runs. These two layers are now joined together using biocompatible pressure sensitive silicone adhesive glue such as Dow Corning BIO-PSA 7-4302 silicone adhesive to form a finished implant 110. Advantageously, this task is automated and performed in layer assembly module 1270. In certain embodiments, this layer assembly module 1270 may include a matched pair of custom-designed multi-well plates (not shown) in which one of the plates of the pair is designed specifically to hold the silicone adhesive layer 116 and the other plate of the pair is designed specifically to hold the polymer layer 118. This would allow the layers to be assembled simply by stacking the plates together such that the layers are joined in the proper orientation wherein the silicone adhesive layer 116 is joined at its upper surface to the lower surface of the polymer layer 118. The layer assembly module 1270 may include a means for dispensing an adhesive onto either one or both of the layers 116 or 118 to fix the two layers together. In alternative embodiments, there may be sufficient cohesion between layers 116 and 118 that an adhesive is not required. The skilled person will recognize that the layer assembly module 1270, like a number of other components of system 1000 (e.g. libraries, mixing containers, holding containers etc.) should be considered an optional component of the system and that it is possible for the layers 116 and 118 to be joined manually with or without adhesive.

Administration of or Using the Two-Layer Ocular Implant

To administer the implant, the subconjunctival matrix implant preferably is placed behind the surface epithelium within the sub-Tenon's space. This is done by a surgical procedure that can be performed in an out-patient setting. A lid speculum is placed and a conjunctival radial incision is made through the conjunctiva over the area where the implant is to be placed. Wescott scissors are used to dissect posterior to Tenon's fascia and the implant is inserted. The conjunctiva is reapproximated using a running 10-0 vicryl suture. The eye has many barriers that do not permit easy penetration of drugs. These include the surface epithelium on the front (cornea) of the eye and the blood/retinal barrier either within the retinal blood vessels or between the retinal pigment epithelium that both have tight junctions. These implants are generally about 1-2 mm in diameter for small rodent (i.e., mouse and rat) eyes, 3-4 mm in diameter for rabbit and human eyes and 6-8 mm in diameter for equine eyes.

In certain embodiments, an applicator device is used to inject the implant into the sub-Tenon's space. Such devices are known in the art and have been used for intraocular injections into the vitreous humor of the eye, particularly in intraocular lens implantation after cataract surgery. In certain embodiments, the device is provided with a retractor that engages the conjunctiva and the surface of Tenon's capsule to produce an opening into the sub-Tenon's space. The device is also provided with a means for pushing the implant into the sub-Tenon's space such that withdrawal of the device allows the surrounding tissues to collapse back into place while holding the implant at the desired location.

Additionally, when the implant is placed near the limbus (i.e., the area where the conjunctiva attaches anteriorly on the eye) to encourage the drug diffusion to enter the cornea, it may be preferable to fixate the matrix implant with one or two absorbable sutures (e.g., 10-0 absorbable vicryl sutures). This is done by making holes with a 30 gauge needle in the peripheral portion of the implant, approximately 250-500 µm away from the peripheral edge of the implant. The holes are made 180 degrees from each other. This is done because subconjunctival matrix implants of this invention, when placed near the cornea, are at higher risk to extrude because of the action of the upper eye lid when blinking. When subconjunctival matrix implants of this invention are placed about 4 mm or more away from the limbus, the sutures are optional.

This matrix implant can deliver therapeutic levels of different pharmaceuticals agents to the eye to treat a variety of diseases. Using a rabbit model, drug released from the implant placed in the eye produces negligible levels of the drug in the blood. This significantly reduces the chances of systemic drug side-effects. This implant design of this invention is prepared by unique methodologies and selections of materials leading to and imparting the unique pharmacological performance properties present in the finished devices.

Lipophilic Agents

In accordance with the present invention, the therapeutic agent or component of the implant may comprise, consists essentially of, or consists of, a lipophilic agent. Such lipophilic agents may be small molecules. Lipophilic agents may be released from the implant by diffusion, erosion, dissolution or osmosis. The drug release sustaining component may comprise one or more biodegradable polymers or one or more non-biodegradable polymers.

In one embodiment, the intraocular implants comprise a lipophilic agent. Lipophilic agents or other agent which may be employed in the implants of the present invention include those taught in US Patent Publication, US20140031408, the contents of which are incorporated herein by reference in its entirety.

In another embodiment, intraocular implants comprise a therapeutic agent or component that comprises a lipophilic agent.

Advantageously, the present implants provide a sustained or controlled delivery of therapeutic agents at a maintained level despite the rapid elimination of the lipophilic agents from the eye. For example, the present implants are capable of delivering therapeutic amounts of a lipophilic agent for a period of at least about 30 days to about a year despite the short intraocular half-lives associated with lipophilic agents. The controlled delivery of lipophilic agents from the present implants permits the lipophilic agents to be administered into an eye with reduced toxicity or deterioration of the blood-aqueous and blood-retinal barriers, which may be associated with intraocular injection of liquid formulations containing lipophilic agents.

The implants may be placed in an ocular region to treat a variety of ocular conditions, such as treating, preventing, or reducing at least one symptom associated with non-exudative age related macular degeneration, exudative age related macular degeneration, choroidal neovascularization, acute macular neuroretinopathy, cystoid macular edema, diabetic macular edema, Behcet's disease, diabetic retinopathy, retinal arterial occlusive disease, central retinal vein occlusion, uveitic retinal disease, retinal detachment, trauma, conditions caused by laser treatment, conditions caused by photodynamic therapy, photocoagulation, radiation retinopathy, epiretinal membranes, proliferative diabetic retinopathy, branch retinal vein occlusion, anterior ischemic optic neuropathy, non-retinopathy diabetic retinal dysfunction, retinitis pigmentosa, ocular tumors, ocular neoplasms, and the like.

Kits in accordance with the present invention may comprise one or more of the present implants, and instructions for using the implants. For example, the instructions may explain how to administer the implants to a patient, and types of conditions that may be treated with the implants.

EXAMPLES

The foregoing description will be more fully understood with reference to the following examples. These examples, are, however, exemplary of methods of making and using certain aspects of the present invention and are not intended to impose limits on the scope of the invention as defined by the appended claims.

Example 1: Administration of a Two-Layer Ocular Implant Containing an Nrf2 Regulator Drug in a Mouse Model of Dry AMD Hydroquinone is known as an oxidant component of cigarette smoke. It has been found that mice treated with hydroquinone may be used as a model of dry AMD (Espinosa-Heidmann et al., *Invest. Ophthal. Vis. Sci.*, 2006, 47-729). Aged male mice (>60 weeks, n=4) are fed a high fat diet (TD 88051; Harlan Teklad) supplemented with 0.8% hydroquinone for a minimum of 8 weeks. Alternatively, hydroquinone can be injected subconjunctivally for up 4 weeks as an alternate model. Other models of macular degeneration including the Y402H CFH transgenic under the control of the ApoE promoter, the Ccl2-/- Cx3cr1-/- mice, the Sod1-/- mice, the OXY rats as well other animal models may also be used.

Implants prepared as described herein are administered to the treated mice. The implants are circular, 2.0 mm in diameter and 1 mm thick and contain the Nrf2 regulator sulforaphane at doses of 10 mg and 30 mg. The sulforaphane content of the implants is determined by dissolving implants in 1 mL of phosphate-buffered saline (PBS; pH 7.4) with intermittent stirring followed by HPLC measurements.

It has been discovered that placement of test implants in the sub-Tenon's space of rodents leads to episcleral clearance of the test substance (Chan, Pridgen and Csaky, 2010, *Exp. Eye Res.* 90, 501). Therefore, surgical placement of the implants is performed by incising the conjunctiva and Tenon's fascia prior to placement of the implants in the sub-Tenon's space as far posteriorly as possible.

The mice are then monitored to determine the release of the drug over time by examining the eye using histology, electroretinography or changes in gene expression in the retinal pigment epithelium or photoreceptors. Confirmation of morphological changes in cells indicating the presence of the drug indicates the effectiveness of the implant in transfer of sulforaphane to from the implant to the surrounding tissues in the process of treating macular degeneration.

Example 2: Release Kinetics of a Lipophilic Drug from a Silicone Ocular Implant

Without wishing to be bound by theory, it is believed that certain drugs, particularly highly lipophilic drugs, recrystallize or otherwise morph into a different crystal form within the matrix of the silicone implant and that this change produces improved ocular penetration relative to direct injections of the "naked" drug. Alternatively the controlled release of smaller particles of highly lipophilic drugs from the silicone adhesive implant also results in improved ocular penetration.

To this end, lipophilic drugs useful in the treatment of ocular disorders may be prepared in the implants of the invention. In this study an experimental ocular implant 2 mm in diameter is prepared which contains between 5-80% by weight of a lipophilic drug. In one instance the drug is solubilized in silicone oil into which it is highly soluble in which crosslinker catalyst is added, the solution is mixed, poured into a Teflon mold of predetermined size and the implants are placed at 100 degrees C. for 30 minute. In a first experiment, the rate of release of the drug from the implant into a solution of phosphate-buffered saline (PBS) is measured over a period of time, e.g., about 24 hours.

In a related experiment, release of the drug from the same implant is monitored over a period of multiple days to months with measurements of the total amount of drug released (μg) from the implant being obtained once each day. Lipophilic drugs may show superior release kinetics.

Example 3: Elution of a Lipophilic Compound from an Episcleral Silicone Implant into Rodent Ocular Tissues and Comparison with Direct Episcleral Injections In a series of experiments, elution of a lipophilic compound from the same 2 mm ocular implant described in Example 2 is investigated following episcleral implantation in rodents and compared with direct episcleral injections of similar doses of the same compound. In animals treated with the ocular implant, a 4 mm punch of tissue comprising sclera, conjunctiva and choroid (SCC) is obtained daily for five days. The amount of drug in the retinal tissue is determined separately. Concentrations of the lipophilic compound (ng/mL) are then determined.

These results provide an indication that the implant of the invention functions as intended. The determination that higher concentrations of a lipophilic ocular drug in ocular tissues can be obtained from the implant relative to direct episcleral injections provides a basis for the prediction that other lipophilic drugs can be used in the implant and will function in a similar manner. It is further predicted on this basis that the implant of the present invention is useful for treatment of the ocular disorders described hereinabove.

EQUIVALENTS AND SCOPE

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any nucleic acid or protein encoded thereby; any method of production; any method of use; etc.) can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control.

Section and table headings are not intended to be limiting.

Various references are cited throughout this specification. Each of these references is incorporated herein by reference in entirety.

What is claimed is:

1. A method for forming a molded two-layer ocular implant, the implant comprising a therapeutic agent for treatment of an ocular condition in a human or veterinary animal, the method comprising:
   (a) dispensing a polymer into a curved depression on a mold body to form a polymer layer, said polymer layer having
      (i) a curved external surface which is in contact with the bottom of the curved depression of the mold body wherein the curved external surface of the polymer layer generally conforms to the radius of curvature of the sub-Tenon's capsule of the eye, and
      (ii) an exposed upper surface, wherein any excess polymer at the perimeter of the curved depression on the top surface of the mold body is trimmed;
   (b) generating a curvature in the exposed upper surface of the polymer layer formed in (a) with a first impression body, said first impression body having a protrusion for generating said curvature, thereby forming a curved polymer layer interface surface;
   (c) curing the polymer layer to completion prior to step (d), thereby providing a hardened curved polymer layer interface surface;
   (d) dispensing a degassed silicone adhesive comprising the therapeutic agent dispersed therein onto the hardened curved polymer layer interface surface thereby providing a silicone drug layer with an exposed surface, and optionally degassing the silicone drug layer while in the mold body;
   (e) generating a curvature in the exposed surface of the silicone drug layer comprising
      (i') contacting said silicone drug layer with a second impression body, said second impression body having a protrusion for generating said curvature and where the fitting of the second impression body places the perimeter of the second impression body substantially centrally within the perimeter of the depression by the first impression body, and
      (ii') optionally trimming any excess silicone drug polymer on the mold body, thereby forming a curved eye-contacting surface in the silicone drug layer, wherein the curved eye-contacting surface of the silicone drug layer generally conforms to the radius of curvature of the sclera of the eye; and
   (f) curing the silicone drug layer formed in steps (d)-(e) thereby forming the molded two-layer ocular implant, wherein the polymer layer of the molded two-layer ocular implant extends circumferentially beyond the silicone drug layer of the molded two-layer ocular implant such that the surface of the circumferential extension of the polymer layer is capable of making contact with the sclera of the eye.

2. The method of claim 1 wherein the implant is circular or oval-shaped.

3. The method of claim 1 wherein the polymer layer is resistant to diffusion of the therapeutic agent from the silicone layer.

4. The method of claim 1 wherein the polymer layer is substantially impermeable to diffusion of the therapeutic agent from the silicone layer.

5. The method of claim 1 wherein the polymer layer and the silicone drug layer are each about 1 mm thick.

6. The method of claim 1 wherein the radius of curvature of the curved eye-contacting surface of the silicone layer ranges from between about 5 mm to about 6 mm.

7. The method of claim 1 wherein the resulting molded implant is circular with a diameter ranging between about 1 mm and 8 mm.

8. The method of claim 1, comprising the step of mixing an agent that blocks lymphatic absorption with the polymer, wherein said mixing occurs prior to step (a).

9. The method of claim 8 wherein the polymer layer includes an agent that blocks lymphatic absorption of the therapeutic agent.

* * * * *